(12) United States Patent
Tobe et al.

(10) Patent No.: US 7,084,164 B2
(45) Date of Patent: Aug. 1, 2006

(54) TRIAZOLE DERIVATIVE

(75) Inventors: Takahiko Tobe, Tsukuba (JP); Takashi Sugane, Tsukuba (JP); Wataru Hamaguchi, Tsukuba (JP); Itsuro Shimada, Tsukuba (JP); Kyoichi Maeno, Tsukuba (JP); Junji Miyata, Tsukuba (JP); Tetsuya Kimizuka, Itabashi-ku (JP); Takeshi Suzuki, Tsukuba (JP); Atsuyuki Kohara, Tsukuba (JP); Takuma Morita, Tsukuba (JP); Michael Arlt, Seeheim Jugenheim (DE); Hartmut Greiner, Weiterstadt (DE)

(73) Assignee: Astellas Pharma, Inc., Tokyo (JP)

( * ) Notice: Subject to any disclaimer, the term of this patent is extended or adjusted under 35 U.S.C. 154(b) by 0 days.

(21) Appl. No.: 11/232,011

(22) Filed: Sep. 22, 2005

(65) Prior Publication Data

US 2006/0025461 A1  Feb. 2, 2006

Related U.S. Application Data

(62) Division of application No. 10/848,386, filed on May 19, 2004, now Pat. No. 7,034,047, which is a division of application No. 10/276,720, filed as application No. PCT/JP01/04128 on May 17, 2001, now abandoned.

(30) Foreign Application Priority Data

May 19, 2000 (JP) ............................ P.2000-148419
Feb. 23, 2001 (JP) ............................ P.2001-47921

(51) Int. Cl.
*A61K 31/41* (2006.01)
*C07D 249/08* (2006.01)

(52) U.S. Cl. ................................. 514/383; 548/265.8

(58) Field of Classification Search ................ 514/383; 548/265.8

See application file for complete search history.

(56) References Cited

U.S. PATENT DOCUMENTS 6,333,326 B1 * 12/2001 Stobie et al. ............... 514/249

FOREIGN PATENT DOCUMENTS

JP  2000-63363 A  2/2000
WO  WO 01/58880 A1  8/2001

OTHER PUBLICATIONS

CA:135:180769 abs of WO 2001058880 Aug. 2001.

* cited by examiner

*Primary Examiner*—Kamal A. Saeed
*Assistant Examiner*—Susannah Chung
(74) *Attorney, Agent, or Firm*—Sughrue Mion, PLLC

(57) ABSTRACT

The invention relates to a triazole derivative with an activity inhibiting glycine transporter and for use as a pharmaceutical drug, and a novel triazole derivative. The inventive triazole derivative has an excellent activity inhibiting glycine transporter and is useful as a therapeutic agent of dementia, schizophrenia, cognitive disorders, or cognitive disorders involved in various diseases such as Alzheimer disease, Parkinson's disease, or Huntington disease or the like, or spasm involved in diseases such as nerve degenerative diseases and cerebrovascular disorders, or the like. Particularly, the pharmaceutical drug is useful for the amelioration of learning disability of dementia and the like.

7 Claims, No Drawings

TRIAZOLE DERIVATIVE

This is a divisional of application Ser. No. 10/848,386 filed May 19, 2004, now U.S. Pat. No. 7,034,047 which is a divisional of application Ser. No. 10/276,720, filed Nov. 18, 2002, (abandoned), which is U.S. national stage application of PCT/JP01/04128, filed May 17, 2001. The entire disclosures of the prior applications, application Ser. Nos. 10/848,386, 10/276,720 and PCT/JP01/04128 are hereby incorporated by reference.

TECHNICAL FILED

The present invention relates to the pharmaceutical composition comprising triazole derivative as an effective ingredient, which is useful as an inhibitor of the activity of glycine transporter, and a novel trizole derivative with an action as an inhibitor of the activity of glycine transporter.

BACKGROUND ART

Glycine is known as an excitatory and inhibitory neurotransmitter in the central and peripheral nervous systems. These functions work via two different types of receptors, in which different types of glycine transporter are independently involved. The function as a inhibitory neurotransmitter works via the strychnine-sensitive glycine receptor present mainly in spinal cord and brain stem. Alternatively, the function as an excitatory neurotransmitter works via N-methyl-D-aspartic acid (NMDA) receptor known as a subtype of glutamate receptors. Glycine is known as a coagonist for the NMDA receptor (Johnson J. W. and Asher P., Glycine potentiates the NMDA response in clutured mouse brain neurons, Nature, 325, 529–531, (1987)). The NMDA receptor is widely distributed in brain, particularly in cerebral cortex and hippocampus.

Neurotransmitter transporter plays a significant role in the control of the concentration of neurotransmitter in the synaptic cleft, by incorporating the neurotransmitter inside the cells. Additionally, it is considered that neurotransmitter transporter makes a contribution to the recycling of neurotransmitter, by incorporating the neurotransmitter into the presynapse terminus. It is considered that the control of the functions of neurotransmitter transporter is useful for therapeutically treating various diseased conditions due to abnormalities in nerve functions, through the control of the concentration of neurotransmitter in the synaptic cleft.

Glycine transporter (GLYT) was first cloned in 1992 (Guastella J., et al., Cloning, expression and localization of a rat brain high-affinity glycine transporter, Proc. Natl. Acad. Sci., 89, 7189–93, 1992). Two types of the transporters, namely GLYT1 and GLYT2, have been identified so far (Liu Q. R., et al., Cloning and expression of a spinal cord- and brain-specific glycine transporter with novel structural features, J. Biol. Chem., 268, 22802–8, 1993). Furthermore, a report tells that GLYT1 has several splicing variants (Kim K. M., et al., Cloning of the human glycine transporter type 1: molecular and pharmacological characterization of novel isoform variants and chromosomal localization of the gene in the human and mouse genomes, Mol. Pharmacol., 45, 608–17, 1994).

GLYT1 is expressed at a high density in spinal cord, brain stem, cerebellum, diencephalon and retina, while GLYT1 is expressed at a low density in olfactory bulb and cerebral hemisphere. It is considered that GLYT1 controls the NMDA receptor function (Smith K. E., et al., Cloning and expression of a glycine transporter reveal colocalization with NMDA receptors, Neuron, 8, 927–35, 1992; Guastella J., et al., Cloning, expression, and localization of a rat brain high-affinity glycine transporter, Proc. Natl. Acad. Sci., 89, 7189–93, 1992; and Bergeron, R., et al., Modulation of N-methyl-D-aspartate receptor function by glycine transport, Proc. Natl. Acad. Sci. USA, 95, 15730–15734, 1998). Javitt, et al. have reported that glycyldodecylamide (GDA) as a glycine transporter inhibitor suppresses the enhancement of activity in mouse as induced by phencyclidine (PCP) as an NMDA receptor antagonist (Javitt D. C., et al., Reversal of phencyclidine-induced hyperactivity by glycine and the glycine uptake inhibitor glycinedodecylaminde, Neuropsychopharmacology, 17, 202–4, 1997).

Alternatively, the expression of GLYT2 is limited to spinal cord, brain stem and cerebellum (Goebel D. J., Quantitative gene expression of two types of glycine transporter in the rat central nervous system, Mol. Brain Res., 40, 139–42, 1996; Zafra F., et al., Glycine transporters are differentially expressed among CNS cells, J. Neurosci., 15, 3952–69, 1995). Thus, it is considered that GLYT2 is involved in the control of the function of strychnine-sensitive glycine receptor. It is suggested that the inhibition of GLYT2 induces the attenuation of pain transmission in spinal cord via the enhancing action of strychnine-sensitive glycine receptor function (Yaksh, T. L., Behavioral and autonomic correlates of the tactile evoked allodynia produced by spinal glycine inhibition: effects of modulatory receptor systems and excitatory amino acid antagonists, Pain, 37, 111–123, 1989).

Furthermore, the enhancement of the strychnine-sensitive glycine receptor function is useful for the therapeutic treatment of abnormal muscular constraction such as spasm, myoclonus and epilepsy (Truong D. D., et al., Glycine involvement in DDT-induced myoclonus. Movement Disorders. 3,77–87, 1988; and Becker, C. M., et al., Disorders of the inhibitory glycine receptor: the spastic mouse, FASEB J. 4, 2767–2774, 1990). Spasm has a relation with nerve disorders and damages such as epilepsy, cerebrovascular disorders, head injuries, multiple sclerosis, spinal injuries and dystonia.

It has been known that NMDA receptor has relations with various diseased conditions. It is suggested that the functional deterioration of NMDA receptor has a relation with schizophrenia (Javitt D. C. and Zukin S. R., Recent advances in the phencyclidine model of schizophrenia, American Journal of Psychiatry, 148, 1301–8, 1991). It is reported that the negative symptoms of schizophrenic patients are ameliorated with a high dose of glycine (Heresco-Levy U., et al., Double-blind, placebo-controlled, crossover trial of glycine adjuvant therapy for treatment-resistant schizophrenia, Br J Psychiatry, 169, 610–7, 1996).

Additionally, the activation of NMDA receptor is involved in the formation of long-term potentiation (LTP) considered as a memory and learning model at the neuron level (Collingridge G. L. and Bliss T. V., NMDA receptors-their role in long-term potentiation. Trends. Neurosci., 10, 288–93, 1987). Still additionally, the administration of an NMDA receptor antagonist to animals induces an amnesia therein (Morris R. G., Andersen E., Lynch G. S. and Braudy M., Selective impairment of learning and blockade of long-term potentiation by an N-methyl-D-aspartate receptor antagonist, AP5, Nature, 319, 774–6, 1986; and Mark J. Benvenga and Theodore C. Spaulding, Amnesic effect of the novel anticonvulsant MK-801, Pharmacol Biochem Behav., 30, 205–207, 1988). Hence, it is suggested that NMDA receptor plays a very significant role in memory and learning.

Further, the deterioration of the function of NMDA receptor has been reported even in humans, namely in patients with Alzheimer-type dementia (Ninomiya, H., et al., binding in human frontal cortex: decreases in Alzheimer-type dementia., J. Neurochem., 54, 526–32, 1990; and Tohgi, H., et al., A selective reduction of excitatory amino acids in cerebrospinal fluid of patients with Alzheimer type dementia compared with vascular dementia of the Binswanger type., Neurosci. lett., 141, 5–8, 1992).

Alternatively, a number of papers report an anti-amnesia action of a glycine-site agonist in animal models (Matsuoka N. and Aigner T. G., D-Cycloserine, apartial agonist at the glycine site coupled to N-methyl-D-aspartate receptors, improves visual recognition memory in rhesus monkeys, J. Exp. Pharmacol. Ther., 278, 891–7, 1996; Ohno M., et al. Intrahippocampal administration of a glycine site antagonist impairs working memory performance of rats. Eur. J. Pharmacol., 253, 183–7, 1994; and Fishkin R. J., et al., D-cycloserine attenuates scopolamine-induced learning and memory deficits in rats., Behav. Neural. Biol., 59, 150–7, 1993). These findings suggest that drugs inhibiting the activity of glycine transporter and thereby activating the function of NMDA receptor are useful as therapeutic agents of dementia, schizophrenia and other cognitive disorders.

As the glycine transporter inhibitor, WO97/45115 disclosing tertiary amins and WO97/45423 disclosing piperidine derivatives (TROPHIX PHARMACEUTICALS INC.), WO99/34790 disclosing amino acid derivatives and WO99/41227 disclosing tricyclic compounds (ALLELIX NEUROSCIENCE INC.), WO99/44596 and WO99/45011 disclosing piperidine derivatives (JANSSEN PHARMACEUTICA N.V.), and WO00/07978 disclosing aminomethylcarbonate derivatives (AKZO NOBEL N.V.) are reported, other than glycyldodecylamide (GDA). As 1,2,4-triazole derivatives, the following compounds are disclosed: DE4302051 (Dr. Karl Thomae G.m.b.h., platlet aggregation inhibitory activity; Iran. J. Chem. Chem. Eng. (1998), 17, 14 (A. Shafiee, et al., antibacterial and antifungal activities), DE3808283 (Boehringer Ingelheim K G., platelet activation factor antagonistic activity), WO97/32873 (Pfizer Research and Development Company N.V., NMDA receptor antagonistic activity), and DD251345 (VEB Chemiekombinat Bitterfeld Ger. Dem. Rep., biocidal activity), Eur. J. Med. Chem. (1985), 20, 257(F. Clemence, et al., analgesic and anti-inflammation activity), Sci. Pharm. (1978), 46, 298 (A. A. B. Hazzaa, et al., anti-spasm action). However, there are no reports that these compounds inhibit glycine transporter activity.

Based on the background described above, the present inventors have made investigations about compounds with potent inhibitory activity of glycine transporter. Consequently, the inventors have found that a specific type of triazole derivative has a potent inhibitory activity of glycine transporter. Thus, the invention has been achieved.

DISCLOSURE OF THE INVENTION

The invention relates to a glycine transporter inhibitor which comprises a triazole derivative represented by the following general formula (I) or a pharmaceutically acceptable salt thereof as the effective ingredient:

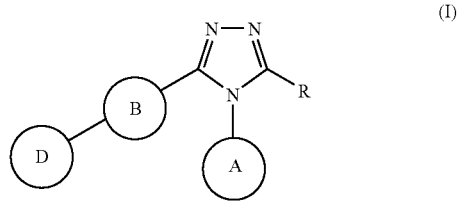

(in the formula, the symbols represent the following meanings;

Ring A:

(1) an aromatic carbon ring which may be substituted, (2) an aliphatic carbon ring which may be substituted and may be condensed with benzene ring or hetero ring, (3) a 5-membered hetero ring which may be substituted and contain one or two nitrogen atoms as the hetero atoms composing the ring and may contain one oxygen atom or sulfur atom as a hetero atom other than the nitrogen atoms and may be condensed with benzene ring or (4) a 6-membered hetero ring which may be substituted and contain one nitrogen atom as a ring atom and may contain one oxygen atom or sulfur atom as a hetero atom other than the nitrogen atom and may be condensed with benzene ring;

Ring B or D may be the same or different and each represents aromatic carbon ring which may be substituted, an aliphatic carbon atom which may be substituted, or a hetero ring which may be substituted.

R: H, halogeno-lower alkyl, aryl which may be substituted, hetero ring which may be substituted, cycloalkyl which may be substituted, or -[Alk1]m-X-[Alk2]n-Y—$R^1$ wherein $R^1$: H, OH, cyano, aryl which may be substituted, hetero ring which may be substituted, cycloalkyl which may be substituted, or lower alkoxyl;

X: bond, oxygen atom, S(O)q, or —N($R^2$)—;

Y: bond, —C(O)—, —C(O)—N($R^3$)—, -$Z_1$-Alk3-, or —N($R^3$)-Alk3—C(O)—, with the proviso that $R^1$ represent other than OH and lower alkoxy, when Y is bond;

Alk1 or Alk2 may be the same or different and each represents lower alkylene, lower alkenylene or lower alkynylene; and m or n may be the same or different and each represents 0 or 1 or m+n=1, provided that X represents bond;

$Z_1$: S(O) q , —N($R^3$)—, —C(O)— or —C(O)—N($R^3$)—;

Alk3: lower alkylene;

$R^2$ or $R^3$: the same or different from each other and each represents H or lower alkyl;

q: 0, 1 or 2 may be)

Additionally, the invention relates to a pharmaceutical composition containing a glycine transporter inhibitor represented by the general formula (I) as the effective ingredient.

The invention furthermore relates to a novel triazole derivative represented by the following general formula (Ia) or a salt thereof.

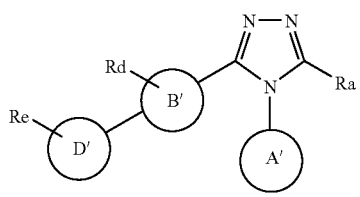

(in the formula, the symbols represent the following meanings;

Ring A':
(1) the group represented by the formula:

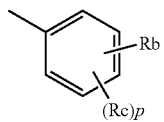

(2) naphthalene which may be substituted with one or two substituents selected from the group represented by Rf,
(3) an aliphatic carbon ring which may be substituted with one or two substituents selected from the group represented by Rf and which may be condensed with benzene ring or hetero ring,
(4) a 5-membered hetero ring which may be substituted with one or two substituents selected from the group represented by Rf and contain one or two nitrogen atoms as the hetero atoms composing the ring and may contain one oxygen atom or sulfur atom as a hetero atom other than the nitrogen atoms and may be condensed with benzene ring; or
(5) a 6-membered hetero ring which may be substituted with one or two substituents selected from the group represented by Rf and which contain one nitrogen atom as the ring atom and may contain one oxygen atom or sulfur atom as a hetero atom other than the nitrogen atom and may be condensed with benzene ring;

Ring B': benzene or nitrogen-containing monocyclic hetero ring; or

Ring D': benzene or hetero ring, provided that ring A', B' and D' never simultaneously represents benzene ring;

Ra: a halogeno-lower alkyl, a hetero ring which may be substituted, cycloalkyl which may be substituted, or -[Alk1]m-X-[Alk2]n-Y—$R^1$ wherein
$R^1$: H, OH, cyano, aryl which may be substituted, hetero ring which may be substituted, cycloalkyl which may be substituted, or lower alkoxyl;
X: bond, oxygen atom, S(O)q, or —N($R^2$)—;
Y: bond, —C(O)—, —C(O)—N($R^3$)—, -$Z_1$-Alk3-, or —N($R^3$)-Alk3—C(O)—, with the proviso that R1 represent other than OH and lower alkoxy, when Y is bond;
Alk1 or Alk2 may be the same or different and each represents lower alkylene, lower alkenylene, or lower alkynylene;
m or n may be the same or different and each represents 0 or 1 or m+n=1, provided that X represents bond;
$Z_1$: S(O)q, —N($R^3$)—, —C(O)— or —C(O)—N($R^3$)—;
Alk3: lower alkynylene;

$R^2$ or $R^3$: the same or different from each other and each represents H, or lower alkyl;
Rb: halogen atom, lower alkyl which may be substituted with the following substituents, lower alkynyl, halogeno-lower alkyl, hetero ring, hetero ring-O—, cyano, nitro, halogeno-lower alkyl-O—, lower alkoxyl, —O-lower alkylene-N($R^3$)-lower alkylene-C(O)O—$R^6$, $Z_2$—$R^6$, or $Z_3$—$R^7$, the substituents of the lower alkyl: OH, cyano, lower alkoxyl, amino which may be substituted with lower alkyl;
$Z_2$: S(O)q, —N($R^3$)—, —C(O)—, —C(O)—N($R^3$)—, —N($R^3$)—C(O)—, —C(O)—S(O)q-, —N($R^3$)—S(O)q-, or —C(O)O—;
$Z_3$: —N($R^3$)—, or —N($R^3$)—C(O)—;
$R^6$: H, lower alkyl or aryl;
$R^7$: OH, or lower alkoxyl;
p: 0 or 1;
q: 0, 1 or 2;
Rc: lower alkyl, or halogen atom;
Rd or Re: the same or different from each other and each represents H, halogen atom, lower alkyl, lower alkoxyl, OH, lower alkyl, halogeno-lower alkyl, phenyl, halogeno-lower alkyl-O—, amino which may be substituted with lower alkyl or —N$R^8$C(O)—$R^9$;
$R^8$ or $R^9$: the same or different from each other and each represents H, or lower alkyl;
Rf: a group represented by Rb, oxo group, or aryl, with the psoviso that Rd represents other than H, when the ring A' represents benzene substituted with lower alkoxyl and the ring B' represents benzene.

Additionally, the invention provides a novel triazole derivative represented by the following general formula (Ib) or a salt thereof.

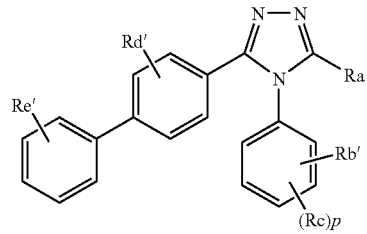

(in the formula, the symbols represent the following meanings:
Ra, Rc or p: the same group as formula (Ia) described in the claim 3;
Rb': halogen atom, lower alkyl which may be substituted with the following substituents, halogeno-lower alkyl, hetero ring, hetero ring-O—, cyano, nitro, halogeno-lower alkyl-O—, lower alkoxyl, —O-lower alkylene-N($R^3$)-lower alkylene-C(O)O—$R^6$, —N($R^3$)—$R^7$, $Z_2$'—$R^6$, or $Z_3$—$R^7$;
the substituents of the lower alkyl: OH, cyano, lower alkoxyl, amino which may be substituted with lower alkyl;
$Z_2$': S(O)q, —C(O)—, —C(O)—N($R^3$)—, —N($R^3$)—C(O)—, —C(O)—S(O)q-, —N($R^3$)—S(O)q-, —C(O)O;
$R^3$, $Z_3$, $R^6$, $R^7$ or q: the same group as formula (Ia) described in the claim 3;
Rd': H, lower alkoxyl, OH or lower alkyl;
Re': H, halogen atom, lower alkoxyl, halogeno-lower alkyl, halogeno-lower alkyl-O—, or N$R^8$C(O)—$R^9$;

R⁸ or R⁹: the same group as formula (Ia) described in the claim 3; with the priviso that, (1). at least one of Rd' or Re' represents a group other than H, when Ra is lower alkyl, p=0:
Rb' represents lower alkyl, lower alkoxyl or halogen atom; or Rd' represents a group except for lower alkyl, provided that Re' is H;

(2). Rb' represents a group other than lower alkyl or lower alkoxyl, when Ra represents α-styryl and Rd' and Re' represent H and p=0;

(3). Rb' represents a group other than lower alkyl, when Ra represents 2-furyl and Rd' and Re' represent H and p=0.)

The invention relates to a triazole derivative represented by the general formula (Ia) or a salt thereof, wherein the ring B' represents nitrogen-containing monocyclic hetero ring; the ring D' is benzene ring; Rf is halogen atom, lower alkyl, lower alkoxyl, aryl, cyano, carbamoyl or oxo group; more preferably, the ring B' is pyridine ring; the ring D' is benzene ring; and the ring A' is 2,1,3-benzooxadiazole, or benzene substituted with one or two substituents selected from lower alkyl, halogen atom or cyano; and most preferably, the triazole derivative is
5-[4-(2,6-difluorophenyl)-5-isopropyl-4H-1,2,4-triazol-3-yl]-2-phenylpyridine;
4-[3-isopropyl-5-(6-phenylpyridin-3-yl)-4H-1,2,4-triazol-4-yl]-2,1,3-benzooxadiazole;
3-[3-(3-methoxypropyl)-5-(6-phenylpyridin-3-yl)-4H-1,2,4-triazol-4-yl]-2-methylbenzonitrile;
3-[3-ethyl-5-(6-phenylpyridin-3-yl)-4H-1,2,4-triazol-4-yl]-2-methylbenzonitrile;
2-{3-[N-(2-methoxyethyl)-N-methylamino]-5-(6-phenylpyridin-3-yl)-4H-1,2,4-triazol-4-yl}benzonitrile;
4-(2,1,3-benzooxadiazol-4-yl)-N-(2-methoxyethyl)-N-methyl-5-(6-phenylpyridin-3-yl)-4H-1,2,4-triazol-3-ylamine
or a salt thereof.

Additionally, the invention relates to a pharmaceutical composition which comprises the triazole derivative of the general formula (Ia) or (Ib) as an active ingredient.

The triazole derivative in accordance with the invention will further be described.

The substituent as described in the phrase 'which may be substituted' specifically includes those described below, unless otherwise stated.

Above mentioned substituted groups are represented by Rb', Rf, Rd and Re, hetero ring groups bound via nitrogen atom, and the like.

Herein, the term 'lower' in the specification represents linear or branched hydrocarbon chain with one to 6 carbon atoms.

Thus, the term 'lower alkyl' means monovalent saturated hydrocarbon, linear or branched, specifically including for example methyl, ethyl, propyl, isopropyl, butyl, isobutyl, s-butyl, t-butyl, pentyl, isopentyl and the like.

The term 'lower alkynyl' represents monovalent, linear or branched unsaturated hydrocarbon with one or more triple bonds with 2 to 6 carbon atoms and with both the termini being of free atomic valence and specifically includes ethynyl, 1-propionyl and the like.

The term 'lower alkylene' represents the saturated hydrocarbon of divalence and with both the termini being of free atomic valence.

The term 'lower alkenylene' represents divalent, linear or branched unsaturated hydrocarbon with one or more double bonds with 2 to 6 carbon atoms and with both the termini being of free atomic valence and specifically includes vinylene, propenylene and the like.

The term 'lower alkynylene' means divalent, linear or branched unsaturated hydrocarbon with one or more triple bonds with 2 to 6 carbon atoms and with both the termini being of free atomic valence.

The term 'lower alkoxyl' specifically includes for example, methoxy, ethoxy, propoxy, isopropoxy, butoxy, isobutoxy, s-butoxy, t-butoxy, pentyloxy, hexyloxy, and isohexyloxy and the like.

'Halogen atom' includes fluorine, chlorine, bromine and iodine.

'Halogeno-lower alkyl' means the lower alkyl substituted with one or more halogen atoms, which is preferably trifluoromethyl and trifluoroethyl.

'Aromatic carbon ring' includes benzene and naphthalene, while the monovalent aromatic carbon ring group is expressed as 'aryl'.

'Aliphatic carbon ring' means 3- to 8-membered monocyclic saturated hydrocarbon ring, while the monovalent group thereof is expressed as 'cycloalkyl'. Preferably, the 'aliphatic carbon ring' is cyclopropyl, cyclopentyl and cyclohexyl.

'Aliphatic carbon ring which may be condensed with benzene ring' means an aliphatic carbon ring condensed with benzene ring and is bound via the carbon atom on the aliphatic carbon ring to other groups. Preferably, the ring is indane and 1,2,3,4-tetrahydronaphthalene.

'Aliphatic carbon ring which may be condensed with hetero ring' means the aliphatic carbon ring condensed with the following hetero ring and is bound via the carbon atom on the aliphatic carbon ring to other groups. Preferably, the ring is 5,6,7,8-tetrahydroquinoline.

'Hetero ring' means aromatic hetero ring, saturated hetero ring and unsaturated hetero ring.

'Aromatic hetero ring' means 5- or 6-membered monocyclic or condensed heteroaryl containing one to 3 hetero atoms selected from nitrogen atom, oxygen atom or sulfur atom and the aromatic hetero ring is bound via the carbon atom or nitrogen atom in the ring to other groups. Preferably, the aromatic hetero ring includes furan, pyrrole, thiophen, pyrazole, thiazole, imidazole, pyridine, pyrimidine, pyrazine, quinoline, isoquinoline and quinoxaline rings and the like.

Herein, the hetero ring represented by Rb or Rb' means those bound via the carbon atom in the ring to benzene ring.

'Saturated hetero ring' means 5- or 6-membered, saturated hetero ring containing one to 3 hetero atoms selected from nitrogen atom, oxygen atom or sulfur atom and is bound via the carbon atom or nitrogen atom in the ring to other groups. Preferably, the saturated hetero ring includes pyrrolidine, piperidine, piperazine and morpholine rings and the like.

'Unsaturated hetero ring' means 5- or 6-membered, unsaturated hetero ring containing double bond in the hetero ring, except for aromatic hetero ring.

'Nitrogen-containing monocyclic hetero ring' means saturated or aromatic 5- or 6-membered monocyclic hetero ring which essentially contains one or more nitrogen atoms as the constitutional elements of the ring and may contain one to 3 hetero atoms selected from oxygen atom or sulfur atom as other hetero atoms, in the 'hetero ring' described above and the 'nitrogen-containing monocyclic hetero ring' is bound via the carbon atom or nitrogen atom in the ring to other groups. Preferably, the nitrogen-containing hetero atom is pyrrole, imidazole, pyrazole, triazole, tetrazole, thiazole, furazan, pyridine, pyrazine, pyrimidine, pyridazine, pyrrolidine, piperidine, piperazine, morpholine and the like. More preferably, the nitrogen-containing monocyclic hetero ring is 5- or 6-membered monocyclic hetero ring where the hetero atom as the constitutional element of the ring is only nitrogen atom and contains one to 3 nitrogen atoms.

'5-membered hetero ring which may contain one or 2 nitrogen atoms as the hetero atoms composing the ring and may contain one oxygen atom or sulfur atom as the hetero atom other than the nitrogen atoms and which may be condensed with benzene ring' as represented by the item (4) for the ring A means, among the hetero rings, a 5-membered hetero ring which may contain 2 or less nitrogen atoms as the constitutional atoms of the ring and may contain one oxygen atom or nitrogen atom other than the atoms, as well as the 5-membered hetero ring in condensation with benzene ring.

The 5-membered hetero ring includes thiazole, furan, pyrrole, imidazole, pyrazole, furazan, thiadiazole, pyrazolidine, benzoimidazole, benzofuran, benzooxadiazole, benzothiadiazole, indole, isoindole, indazole and the like.

'6-membered hetero ring which may contain one nitrogen atom as the ring atom and may contain one oxygen atom or sulfur atom as a hetero atom other than nitrogen atom and which may be condensed with benzene ring' as represented by the item (4) for the ring A means, among the hetero rings, a 6-membered hetero ring which may contain nitrogen atom within one in number as the ring-composing atom and may contain one oxygen atom or sulfur atom other than the atom described above-mentioned the hetero ring, as well as the 6-membered hetero ring in condensation with benzene ring.

The 6-membered hetero ring includes morpholine, pyridine, piperidine, quinoline, isoquinoline, 1,2-dihydroisoquinoline and 1,2,3,4-tetrahydroisoquinoline.

The compound for use as the effective ingredient of the pharmaceutical composition of the invention can sometimes form a salt with an inorganic acid or an organic acid. The salt thereof has an action to inhibit the activity of glycine transporter. The preferable salt includes for example salts thereof with mineral acids such as hydrochloric acid, hydrobromic acid, hydroiodic acid, sulfuric acid, nitric acid or phosphoric acid or the like; salts thereof with organic acids such as formic acid, acetic acid, propionic acid, oxalic acid, malonic acid, succinic acid, fumaric acid, maleic acid, lactic acid, malic acid, tartaric acid, citric acid, carbonic acid, glutamic acid, aspartic acid, methanesulfonic acid or ethanesulfonic acid or the like; salts thereof with inorganic bases such as sodium, potassium, magnesium, calcium or aluminum or the like; salts thereof with organic bases such as methylamine, ethylamine or ethanolamine or the like; and salts thereof with basic amino acids such as lysine or ornithine or the like. Additionally, the compound can form tertiary ammonium salt when the compound reacts with lower alkyl halide, lower alkyl triflate, lower alkyl tosylate or benzyl halide or the like. As such tertiary ammonium salt, the salt of the compound with methyl iodide or benzyl chloride or the like is preferable.

The compound for use as the effective ingredient in the pharmaceutical composition of the invention includes optical isomers based on the asymmetric carbon atoms, geometric isomers based on the double bonds or cyclohexane ring, and atropeisomers occurring due to the inhibition of the rotation around a certain single bond. When two or more asymmetric carbon atoms are present, furthermore, the compound includes diastereomers. These various types of isomers isolated and mixtures of these isomers are also encompassed within the scope of the invention. Furthermore, the compound of the present invention includes hydrates, various solvates and tautomeric isomers. Still further, the compound for use as the effective ingredient of the inventive pharmaceutical composition includes compounds of crystal polymorphism. All these crystal forms are also encompassed within the scope of the compound for use as the effective ingredient of the pharmaceutical composition of the invention.

Further, the compound of the present invention includes pharmacologically acceptable prodrugs. The group forming the pharmaceutically acceptable prodrugs of the compound of the present invention includes the group described in Prog. Med. 5; 2157–2161 (1985) and the group described in "Development of pharmaceutical products", Vol. 7, Molecular designing, pp. 163–198, Hirokawa Shoten, 1990. More specifically, the group can be converted to the primary amine, secondary amine, OH or COOH group, through hydrolysis or solvated decomposition or under physiological conditions and include for example lower alkylene —COOR (R represents H or lower alkyl; the same is true hereinbelow) which may be substituted with —OCO—, lower alkenylene-COOR which may be substituted with —OCO—, aryl which may be substituted with —OCO—, —OCO-lower alkylene-O-lower alkylene-COOR, —OCO—COR, lower alkyl which may be substituted with —OCO—, lower alkylene-COOR which may be substituted with —OSO$_2$—, —O-futazyl, 5-methyl-1,3-dioxolen-2-on-4-yl-methyloxy.

Herein, the following compounds are included among preferable examples of known compounds encompassed within the invention of use. For example, the following compounds among the compounds disclosed in Japanese Patent Laid-open No. 2000–63363 are included:

2-[3-(biphenyl-4-yl)-5-methyl-4H-1,2,4-triazol-4-yl]phenol, 3-(biphenyl-4-yl)-4-(2-ethoxyphenyl)-5-methyl-4H-1,2,4-triazole, 3-(biphenyl-4-yl)-5-methyl-4-(2-propoxyphenyl)-4H-1,2,4-triazole, 3-(biphenyl-4-yl)-5-ethyl-4-(2-methoxyphenyl)-4H-1,2,4-triazole, 4-(2-methoxyphenyl)-3-methyl-5-(2'-methylbiphenyl-4-yl)-4H-1,2,4-triazole and 3-(biphenyl-4-yl)-4-(2-iodophenyl)-5-methyl-4H-1,2,4-triazole.

Other than those described above, for example, 3-(biphenyl-4-yl)-5-(furan-2-yl)-4-phenyl-4H-1,2,4-triazole (LTPBP42, CD-ROM catalog 1996), 3-(biphenyl-4-yl)-4-(2-methoxyphenyl)-5-methyl-4H-1,2,4-triazole (LTPBP20, CD-ROM catalog 1996) commercially available from LaboTest Co. (Freiberg, Germany) and the like are also included.

(Production Process)

The production process of the compound in accordance with the invention is now described below.

The objective 3,4,5-tri-substituted-1,2,4-triazole derivative can be synthetically prepared by the following processes. But the production process of the compound of the present invention is not limited to them.

Production Processes Nos. 1 to 3

Prodution Processes No. 1

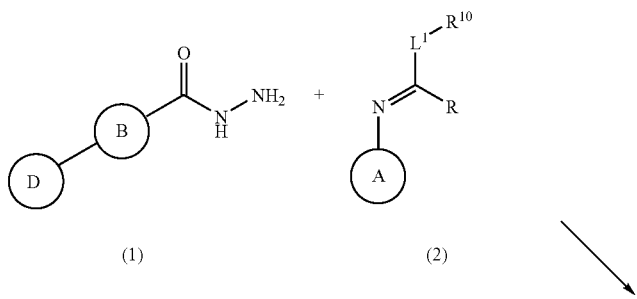

(1)    (2)

Prodution Processes No. 2

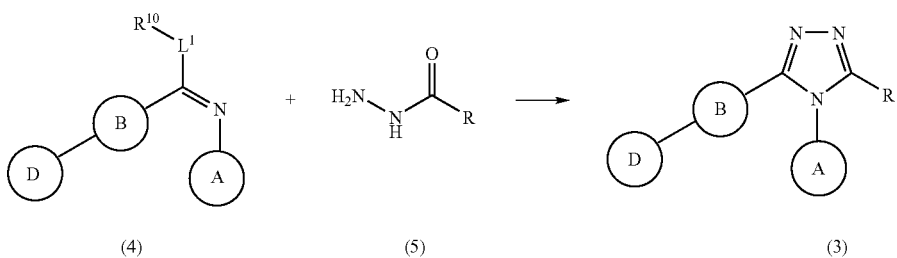

(4)    (5)    (3)

Prodution Processes No. 3

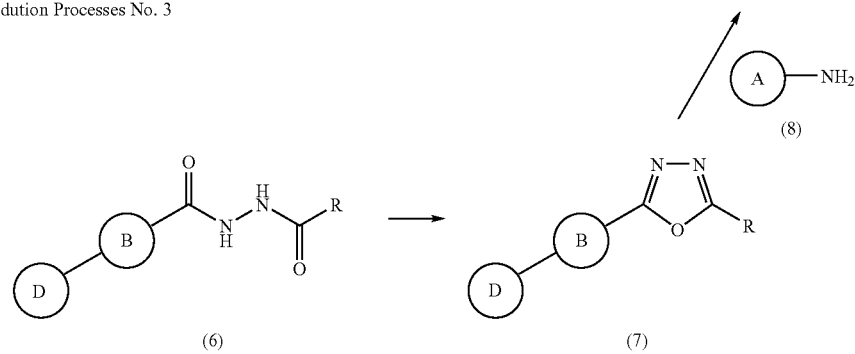

(6)    (7)

(8)

(In the formula, $L^1$ represents oxygen atom or sulfur atom; $R^{10}$ represents lower alkyl and the like. The remaining symbols represent the same as described above. The same is true hereinbelow.)

At the production processes Nos. 1 to 3, the objective 3,4,5-tri-substituted-1,2,4-triazole can be prepared in an almost similar fashion to the method described for example in the unexamined publication (Japanese Patent unexamined publication No. 2000–63363).

According to the production process No. 1, the objective 3,4,5-tri-substituted 1,2,4-triazole derivative can be prepared by subjecting acid hydrazide (1) commercially available or possibly prepared by an almost similar method to the method described in Japanese Patent unexamined publication No. 2000–63363 and the compound (2) to nucleophilic substitution reaction and dehydration cyclarization reaction.

According to the production process No. 2, the compound of the present invention can be prepared by subjecting the compound (4) possibly prepared by an almost similar method to the method described in Japanese Patent Laid-open No. 2000–63363 and acid hydrazide (5) to nucleophilic substitution reaction and dehydration cyclarization reaction.

According to the production process No. 3, the compound of the present invention can be prepared by subjecting 1,3,4-oxadiazole (7) prepared by dehydration cyclarization reaction of diacylhydrazine (6) to reaction with appropriate amine derivative (8).

Production Processes Nos. 4 and 5

Prduction Processes No. 4

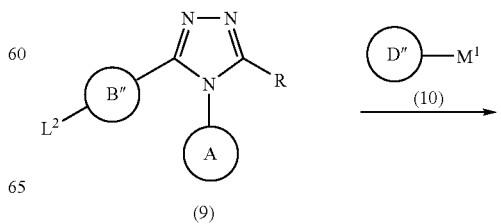

(9)    (10)

Production Processes No. 4

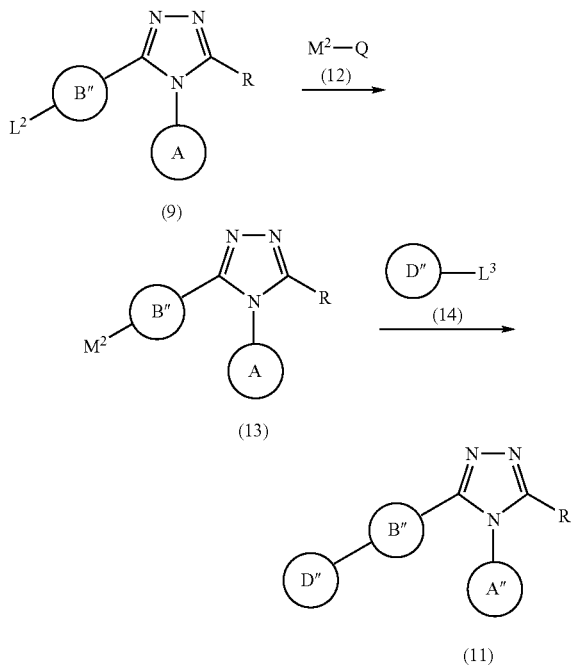

(In the formula, $L^2$ and $L^3$ represent halogen, alkyl- or aryl-sulfonyloxy such as trifluoromethanesulfonyloxy, and phosphoryloxy substituted with lower alkoxy group; $M^1$ and $M^2$ represent metals such as magnesium, zinc, boron and tin and the like; $M^2$-Q represents organic metal compounds and metal halides, for example, described in the reference edited by Tsuji Jiro (Senikinzoku Ga Hiraku Yukigosei, p. 25–p. 37 (1997)) and the like; and B" represents an aromatic carbon ring or aromatic hetero ring; and D" represents an aromatic carbon ring or aromatic hetero ring.)

The 1,2,4-triazole derivative (11) with aromatic rings as the rings B" and D" can be synthetically prepared, using the following production processes Nos. 4 and 5, in addition to the production processes Nos. 1, 2 and 3.

The production process No. 4 is a production process, utilizing the cross coupling reaction between compound of the present invention (9) with halogen or alkylsulfonyloxy as the substituent $L^2$ on the aryl or heteroaryl ring B" and appropriate aryl metal or heteroaryl metal compound (10). Additionally, the production process No. 5 is a production process, utilizing the cross coupling reaction between aryl metal or heteroaryl metal compound (13) prepared from 1,2,4-triazole derivative (9) and aryl or heteroaryl compound (14) with appropriate halogen or alkylsulfonyl group.

The cross coupling reaction in the production processes Nos. 4 and 5 can be performed in an appropriate solvent such as tetrahydrofuran and N,N-dimethylformamide in the presence of palladium compound or nickel compound (for example, tetrakistriphenylphosphine palladium) and in the presence or absence of abase, if necessary, under cooling or heating, using an aryl metal or heteroaryl metal compound (10 or 13) containing magnesium, zinc, boron and tin and the like and an aryl or heteroaryl compound (9 or 14) with an appropriate halogen or an alkylsulfonyloxy group as the raw materials.

Production Process No. 6

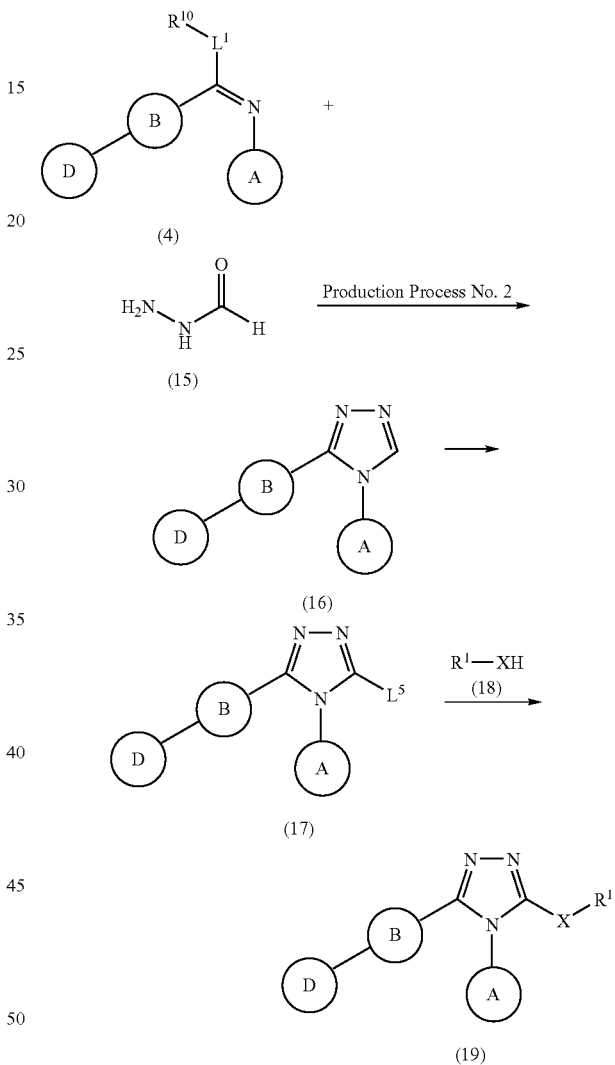

(In the formula, $L^5$ represents an leaving group such as halogen and the like and X represents $NR^2$ or oxygen atom.)

The 1,2,4-trizole derivative (19) with a substituent binding via nitrogen atom or oxygen atom at position 5 can also be prepared by converting the 1,2,4-triazole derivative (16) synthetically prepared by the production process No. 2 into the compound (17), for example, according to the method described by Walser, et al. (Journal of Heterocyclic Chemistry, 12, 717(1975)) and subjecting amine or alcohol derivative (18) to reaction without any solvent or in an appropriate solvent (for example, xylene) in the presence or absence of an appropriate base at 50 to 200° C. for 2 to 72 hours.

Production Process No. 7

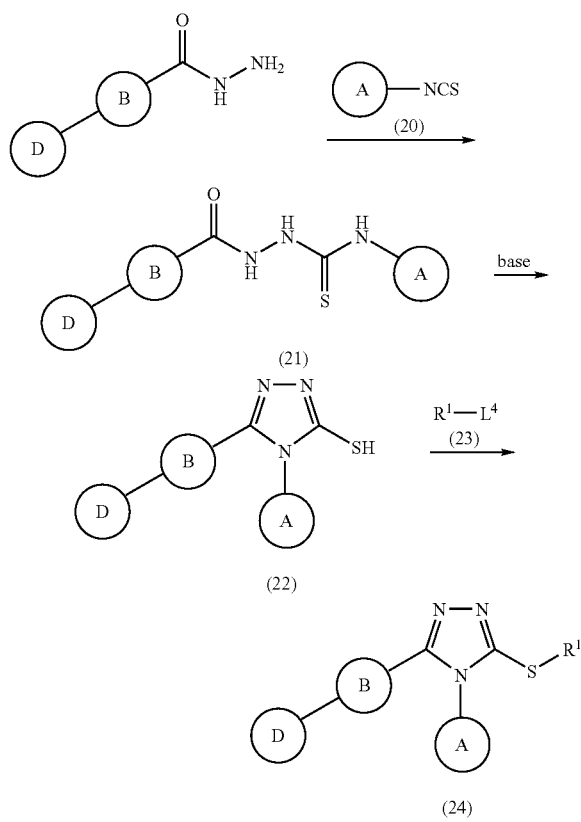

(In the formula, the base represents sodium hydroxide and the like; $L^4$ represents an leaving group such as halogen and the like.)

The 1,2,4-triazole derivative (24) with a substituent binding via sulfur atom at the position 5 can also be prepared, using acid hydrazide (1) commercially available or prepared by a similar method to the method described in Japanese Patent unexamined publication No. 2000-63363 as a raw material, for example according to the method of Maxwell, et al. (Journal of Medicinal Chemistry, 27, 1565 (1984)).

As described above, the compound of the present invention includes isomers such as racemic compounds, optically active compounds and diastereomers and the like, being present singly or in mixture. The racemic compounds can be introduced into stereochemically pure isomers, using appropriate raw material compounds or by general racemic resolution processes (for example, a process of optical resolution, comprising introducing the raw material compounds into diasteromer salts with general optically active acids (tartaric acid, etc.)). Additionally, diastereomer mixtures can be separated by general methods, for example fractional crystallization or chromatography or the like.

PHARMACOLOGICAL TESTS

The pharmacological actions of the compound of the present invention are described hereinbelow.

The action of the compound of the present invention to inhibit the activity of the glycine transporter was verified by the following test methods.

1. Action of Inhibiting Glycine Transporter (Cell Culture)

C6 glioma cell expressing GLYT1 subtype of the glycine transporter (see Gomeza-J., Zafra-F., Olivares-L., Gimenez-C., Aragon-C., Regulation by phorbol esters of the glycine transporter (GLYT1) in glioblastoma cells., Biochim-Biophys-Acta., 1233, 41–46 (1995)) was used.

C6 glioma cell (American Type Culture Collection) was cultured in DMEM containing 10% fetal bovine serum, 100 units/ml penicillin G and 0.1 mg/ml streptomycin sulfate in a $CO_2$ incubator under conditions of 5% $CO_2$ and 37° C.

([$^3$H]-glycine Uptake Assay)

[$^3$H]-glycine uptake was performed by the method of Gomeza, et al.

$C6$ glioma cells were plated out at a concentration of $2 \times 10^4$ cells/well in a 96-well plate (Culturplate, Packard Co.), for culturing for 2 days. Subsequently, [$^3$H]-glycine uptake was tested. The cell was rinsed once in a buffer (150 mM NaCl, 5 mM KCl, 1 mM $CaCl_2$, 1 mM $MgCl_2$, 10 mM glucose, 5 mM L-alanine, 10 mM Hepes-Na, pH 7.4), followed by subsequent addition of the buffer, for incubation at 37° C. for 10 minutes.

After incubation, the buffer was exchanged to a reaction buffer including [$^3$H]-glycine (about 0.2 μM, 41 Ci/mmol, New England Nuclear) and a compound to be assessed, for incubation at 37° C. for another 20 minutes. After 20-min reaction, the reaction mixture was rinsed in ice-cold PBS (phosphate buffered saline). The cell was dissolved in 0.1N NaOH solution, to assay the radioactivity incorporated with a liquid scintillation counter. The specific incorporation was defined as a portion substituted with 3 mM sarcosine in the total incorporation. The test compound was assessed by determining the incorporation-inhibiting ratio of the specific incorporation.

Consequently, the compound of the present invention was verified to have an action to inhibit [$^3$H]-glycine incorporation.

| Test compound | GLYT-inhibiting activity IC50(μM) |
|---|---|
| Compound 1 | 1.0 |
| Compound 2 | 4.6 |
| Compound 3 | 0.35 |
| Production Example 1 | 0.36 |
| Example 1 | 0.14 |
| Example 2 | 0.10 |
| Example 5 | 0.41 |
| Example 6 | 0.26 |
| Example 8 | 0.25 |
| Example 9 | 0.33 |
| Example 10 | 0.20 |
| Example 112 | 1.0 |
| Example 157 | 1.5 |
| Example 202 | 1.6 |
| Example 236 | 0.94 |
| Example 256 | 0.086 |
| Example 279 | 4.6 |

Compound 1:
3-(biphenyl-4-yl)-4-(2-methoxyphenyl)-5-methyl-4H-1,2,4-triazole (Japanese Patent unexamined uplication No. 2000-63363; Example 33)

Compound 2:
3-(biphenyl-4-yl)-5-(furan-2-yl)-4-phenyl-4H-1,2,4-triazole (LTPBP42 CD-ROM catalog 1996 of LaboTest Co. (Freiberg, Germany))

Compound 3:
3-(biphenyl-4-yl)-5-ethyl-4-(2-methoxyphenyl)-4H-1,2,4-triazole (Japanese Patent unexamined publication No. 2000-63363; Example 23)

2. Experimental Method of (+)-HA966-Induced Enhancement of Activity in Mouse the method reported previously (J. Neural Transm., 97: 175–185, 1994) was used for carrying out the experiment with modification.

Animal: male ICR mouse (Nippon SLC; age 5 to 7 weeks)
Chemical drug: reserpine (Apoplon Injection of 1 mg/ml; manufactured by Daiichi Pharmaceuticals Co., Ltd.), (+)-HA966 (Proc. Nat. Acad. Sci. U.S.A., 87, 347–351, 1990), α-methyl-para-tyrosine methyl ester (Sigma, Inc.).
Experimental Apparatus: Supermex (Muromachi Machine)

Experimental Method
(1) Pharmaceutical drug-treated groups were defined as follows.
(16 mice per one group were used for the experiment).
(ACSF+Vehicle) group
{(+)-HA966 80 μg/mouse icv+Vehicle} group
{(+)-HA966 80 μg/mouse icv+test compound} group
(2) 19 hours before (+)-HA966 administration, reserpine (10 mg/kg) was dosed intraperitoneally.
(3) 0.5 hour before (+)-HA966 administration, α-methyl-para-tyrosine methyl ester (250 mg/kg) was intraperitoneally administered.
(4) 20 minutes before (+)-HA966 administration, a test compound was orally given.
(5) (+)-HA966 was acutely administered bilaterally into the lateral ventricule (with free hands using 2-step needle); immediately thereafter, each animal was placed in the measuring cage of an activity measurement apparatus.
(6) Immediately thereafter, the activity per one hour was measured.
(7) The integral value of the activity per one hour was selected as the data. The effect was determined as follows. The enhancement of the activity due to (+)-HA966 {difference between ((+)-HA966+Vehicle)administration group and (ACSF+Vehicle)administration group} was defined as 100%. And the activity in a pharmaceutical drug-treated group {difference between ((+)-HA966+test conpund)administration group and (ACSF+test compound)administration group} was normalized. It was calculated by following formula. When the normalized activity was below 50%, the test compound was judged to have the effect.

The formula used for standardization

{activity of ((+)-HA966+test conpund)administration group−activity of (ACSF+test compound)administration group}÷{activity of ((+)-HA966+Vehicle)administration group−activity of (ACSF+Vehicle)administration group}×100(%)

When the compound shown in the Production Example 1 was orally given at 10 mg/kg, the activity was at 43%.

3. (+)-HA966-Induced Learning Disability (Mouse Passive Avoidance Test)

Animal: male ddY mouse (Nippon SLC; age 7 to 9 weeks at training) was used. 16 to 32 animals were used per one group.

<Experimental Procedures>

Preparation of Pharmaceutical Drugs
(1) A test compound for oral administration was suspended in aqueous 0.5% methyl cellulose solution, and for intraperitoneal administration was suspended in solution dissolved 0.5% of methyl cellulose solution in saline (hereinafter referred to as 0.5% methyl cellulose solution). The administration volume was 10 ml per 1 kg·body weight. As a placebo of the test compound, 10 ml per 1 kg·body weight of aqueous 0.5% methyl cellulose solution for oral administration and 10 ml of aqueous 0.5% methyl cellulose solution (herein referred to as vehicle) for intraperitoneal administration (herein referred to as vehicle) was administrated.
(2) (+)-HA966 was dissolved in artificial cerebrospinal fluid (ACSF). The administration volume was 4 μl per one mouse. As a vehicle of (+)-HA966, 4 μl of ACSF was dosed per one mouse.

Intracerebral Cannula Apparatus 7 to 14 days before the initiation of training, a cannula for intracerebroventricular administration was inplanted to the animals under anesthesia.

Training
(1) On day 1 at the learning experiment, the mice were acclimated in an experimental room for one hour or longer.
(2) A test compound or the vehicle was orally or intraperitoneally given.
(3) 20 minutes thereafter, (+)-HA966 was administered at 60 μg intracerebroventricullaly.
(4) 15 minutes after the dosing of (+)-HA966, the each mouse was placed in the bright room of the experimental apparatus of the passive avoidance reaction test, where the mouse was left for 30 seconds. Subsequently, the guillotine door was opened. When the mice entered in the dark room, the mice were exposed to an electric shock at an intensity of 60V and a delay of 1 sec for a duration of 2 sec. When the mice thus returned to the bright room, the guillotine door was closed. Then, the mice were left in the bright room for 30 seconds.
(5) The mice were taken out to be back to the home cage.
(6) After the termination of the training, the mice were left to stand in the experimental room and were then back to the feeding room.

Test (24 Hours after the Training)
(1) The animals were left in the experimental room for one hour or longer.
(2) After the mice were placed in the bright room and left for 30 seconds, the guillotine door was opened.
(3) The time (step-through latency) required for the mice to cross the sensor of the dark room from the opening of the guillotine door was counted. The longest time for the measurement was 300 seconds.
(4) The step-through latency was adopted as an indicator of learning ability. The learning disability due to (+)-HA966 was compared between the two groups, namely (ACSF+Vehicle) group and {(+)-HA966+Vehicle} group by the Wilcoxon rank sum test. The action of an assessment compound on the improvement of leaning disability was compared between many groups, namelyf{(+)-HA966+Vehicle} group and {(+)-HA966+assessment compounds} groups by the two-tailed Steel test. A significance was determined at $p<0.05$.

The compound shown in the Production Example 1 as dosed intraperitoneally was at the minimum effective dose of 3 mg/kg.

4. Electric Convulsion Shock (ECS)-Induced Learning Disability (Mouse Passive Avoidance Test)

With reference to the previous report (Eur J Pharmacology, 321; 273–278, 1997), assessment was done as follows.

Animal: male ddY mouse (Nippon SLC; age 5 weeks at training) was used. 16 animals were used per one group.

<Experimental Procedures>

Preparation of Chemical Agents

A test compound for oral administration was suspended in aqueous 0.5% methyl cellulose solution, and for intraperitoneal administration was suspended in solution dissolved 0.5% of methyl cellulose solution in saline The dose administered was 10 ml per 1 kg·body weight. As a placebo of the test compound, 10 ml of aqueous 0.5% methyl cellulose solution for oral administration and 10 ml of 0.5% methyl cellulose solution in saline for intraperitoneal administration (herein referred to as vehicle) was administrated.

Training (1) On day 1 at the experiment, the mice were left in an experimental chamber for one hour or longer.

(2) The mice were placed in the bright room of the experimental apparatus of the passive avoidance test, where the mice were left to stand for 30 seconds. Subsequently, the guillotine door was opened. When the mice entered in the dark room, the mice were exposed to an electric shock at an intensity of 60V and a delay of 1 sec for a duration of 2 sec. When the mice thus returned to the bright room, the guillotine door was closed. Then, the mice were left to stand in the bright room for 30 seconds.

(3) The mice were taken out. An electrode was attached on both the ears immediately (within one minute), to give ECS (electric convulsion shock).

(4) A test compound was administered orally or intraperitoneally.

(5) The mice were back to the home cage.

(6) After the termination of the training, the mice were left in the experimental room for 60 minutes or longer and were then back to the feeding room.

Test (24 Hours after the Training)

(1) The animals were left in the experimental room for one hour or longer.

(2) After the mice were placed in the bright room and left for 30 seconds, the guillotine door was opened.

(3) The time (step-through latency) required for the mice to cross the sensor of the dark room from the opening of the guillotine door was counted. The longest time for the measurement was 600 seconds.

(4) The step-through latency was adopted as an indicator of learning ability. The learning disability due to ECS was compared between the two groups, namely (ECS−no load+Vehicle) group and (ECS load+Vehicle) group by the Wilcoxon rank sum test. The action of a test compound on the improvement of leaning disability was compared between many groups, namely (ECS load+Vehicle) group and (ECS load+assessment) compounds groups by the two-tailed Steel test. A significance was determined at p<0.05.

The compound shown in the Production Example 1 as dosed intraperitoneally was at the minimum effective dose of 10 mg/kg.

5. Action of Assessment Compound on Learning Disability in Aged Rat (Water Maze Task).

[Experimental method]

The experimental protocol was defined as follows, with reference to the method of Baxter M., et al. (Neurobiol. Aging 15, 207–213, 1994).

Male F344 rats (Nippon Charles River) of age 24±1 months (aged rats) were used at the experiment. Water (25° C.) was charged in a circle pool of a diameter of 130 cm and a height of 40 cm to a depth of 25 cm, in which a plastic platform of a diameter of 10 cm and a height of 24 cm was arranged to a depth of about 1 cm below the water surface. During the test, water in the pool was made completely opaque, using black ink.

Handling: 3-min handling was carried out twice for all the rats, prior to the experiment.

Shaping: a platform was placed in an alley with a 15-cm width, a 35-cm height (from the water surface) and a 100-cm length. Black opaque water was charged therein so as to place the platform to a depth of about 1 cm below the water surface. The platform was placed the end of the alley. Each rat was placed at a specific place in the alley, allowed to reach the platform. Three successive start locations, each transfer away from the platform, were used; (a) on the platform, (b) with forepaws om the platform, (c) approximately 25 cm from the platform. After the rat climbs on the platform, the rat is retained there for about 10 seconds.

Straight swim: rats are placed on the end of the alley (the opposite side of the platform), to allow the rats to swim three times. When the rats reach the platform, the rats are retained on the platform for about 10 seconds. The latency until the rats reach the platform is recorded.

Acquisition task: rats are gently placed in water, while the rats face on the pool wall so as to subject the rats to acquisition trial at 5 times/day at maximum for the longest duration of 8 days. The latency until the rats reach the platform is recorded with a color video tracking system (Compact VAS) on a computer system. The duration per one trial is set to 60 seconds at maximum. When the rats cannot find the platform within 60 seconds, the experimental person allows the rats to climb the platform. The rats are retained on the platform within about 10 seconds. The trial interval is set to about 2 minutes. The start position (at 7 sites) should be changed every trial in a random manner. For the acquisition trial, 40 trials in total are carried out at maximum. On the first day, the rats are allowed to swim with no dosing of any drug, so as to group the rats evenly on the basis of the latency period. Thereafter, a test compound or the vehicle is dosed for 7 days, to measure the latency period.

Transfer task: about 4 hours after the last trial, 50-sec transfer task is conducted in the absence of platform. Swim time on the targeted quadrant (quadrant of the pool where the platform was present at acquisition task) was measured.

Treatment with pharmaceutical drug: a test compound is suspended in 0.5% MC physiological saline. The pharmaceutical drug and the vehicle of 1 mg/kg were administered intraperitoneally 30 minutes prior to the training. No administration prior to the transfer task.

Using the latency at the acquisition task and the time period in which the rats are retained in the target quadrant of the transfer task as markers, the difference between the test compound and the vehicle is compared by two-way ANOVA or Student t-test.

The efficucy of the compound of present invention on the learning impairment in aged rats can be verified using the water maze Additionally, the efficacy of the compound of the present invention on the learning impairment in aged rats can be verified, using as the object recognition test, as shown in for example the previous report (Pharmacological Research, 36(6); 463–469, 1997).

A pharmaceutical composition containing one or two or more types of the compound represented by the general formula (I) and the pharmaceutically acceptable salt thereof or hydrate thereof as the effective ingredient can be prepared into tablets, powders, fine granules, granules, capsules, pills, liquids, injections, suppositories, ointments, and paps and the like, using carriers and excipients for general use for formulation, and other additives. The resulting formulations are orally or parenterally given.

The clinical dose of the compound of the present invention to humans is appropriately determined, depending on the symptom, age, sex and body weight of an individual patient, to which the compound of the present invention is applied. Generally, the compound of the present invention is orally given at 0.1 to 500 mg per one adult per day in one portion or divided portions. Because the dose varies under various conditions, a dose below the range of the dose may sometimes be sufficient.

As the solid composition for oral administration in accordance with the invention, tablets, powders and granules are used. For such solid composition, one or more active substances are mixed with at least one inactive diluent, for example lactose, mannitol, glucose, hydroxypropyl cellulose, microcrystalline cellulose, starch, polyvinylpyrrdlidone, metasilicate aluminate magnesium and the like.

According to general methods, the composition may satisfactorily contain additives other than inactive diluents, for example lubricants such as magnesium stearate, disintegrators such as cellulose calcium glycolate, stabilizers such as lactose, solubilization or dissolution-auxiliary agents such as glutamic acid or aspartic acid. If necessary, the tablets or pills may be coated with films of substances dissolvable in stomach or intestine, such as sucrose, gelatin, hydroxypropyl cellulose and hydroxypropylmethyl cellulose phthalate and the like.

The liquid composition for oral dosing contains pharmaceutically acceptable emulsifiers, solubilizers, suspending agents, syrups, and elixirs and the like and contains inactive diluents for general use, for example distilled water and ethyl alcohol. The composition may satisfactorily contain auxiliary agents such as solubilization- or dissolution-auxiliary agents, moisturizers and suspending agents, sweeteners, flavoring agents, aromatic agents and preservatives.

The injections for parenteral dosing encompass aseptic, aqueous or non-aqueous solubilizers, suspending agents and emulsifiers. The diluents of aqueous solubilizers and suspending agents include for example distilled water for injections and physiological saline. Water-insoluble solubllizers and suspending agents include for example propylene glycol, polyethylene glycol, vegetable oils such as olive oil, alcohols such as ethyl alcohol, surfactants such as polysorbate 80 (trade name). Such composition may satisfactorily contain additives including isotonic agents, preservatives, moisturizers, emulsifiers, dispersants, stabilizers (for example, lactose), and solubilization- and dissolution-auxiliary agents (for example, glutamic acid and aspartic acid). These may be sterilized by filtration through for example filter with bacteria retained thereon, blending with sterilizers or irradiation. These may be prepared into aseptic solid compositions. The resulting aseptic compositions are used, after dissolution in aseptic water or aseptic solvents for injections prior to use.

EXAMPLES

As to the novel compound of the invention, the invention is now described in more detail in the following Production Examples and Examples. Herein, the invention is not limited to these compounds alone. Further, the raw materials for use in accordance with the invention are described in Reference Examples, in case that the raw materials are novel.

Reference Example 1

N-(2-Fluorophenyl)-2-methylthiopropionimidate methyl ester (1) 2-Fluoroaniline (5.07 g) and triethylamine (9.54 ml) were dissolved in tetrahydrofuran (50 ml), followed by addition of a solution of isobutyryl chloride (5.02 ml) in tetrahydrofuran (20 ml) under ice cooling, and stirred at ambient temperature for 4 hours. After the reaction solution was concentrated under reduced pressure, water (200 ml) was added to the resulting residue, and stirred at ambient temperature for one hour. The resulting solid was filtered and washed with water, to afford N-(2-fluorophenyl)isobutylamide in pale yellow solid (7.08 g, 86%). The physicochemical values are as follows.

$^1$H-NMR (CDCl$_3$) δ: 1.28 (6H, d, J=6.8 Hz), 2.50–2.64 (1H, m), 6.99–7.15 (3H, m), 7.37 (1H, brs), 8.32–8.38 (1H, m).

(2) N-(2-Fluorophenyl)isobutylamide (7.08 g) was dissolved in toluene (90 ml), followed by addition of the Lawesson reagent (8.15 g), and refluxed under heating for one hour. After the reaction solution was cooled to ambient temperature, the solution was concentrated under reduced pressure. The resulting residue was purified by silica gel column chromatography (eluent: n-hexane/ethyl acetate=9/1), to afford N-(2-fluorophenyl)thioisobutylamide as yellow oil (7.74 g, quantitative). The physicochemical values are as follows.

$^1$H-NMR (CDCl$_3$) δ: 1.37 (6H, d, J=6.8 Hz), 2.94–3.08 (1H, m), 7.11–7.25 (3H, m), 8.53–8.65 (2H, m).

(3) N-(2-Fluorophenyl)thioisobutylamide (7.71 g) was dissolved in acetonitrile (150 ml), followed by addition of potassium carbonate (16.2 g) and methyl iodide (7.30 ml), and stirred at 50° C. for 30 minutes. After the reaction solution was cooled to ambient temperature, the resulting solution was concentrated under reduced pressure. To the resulting residue were added water (100 ml) and saturated aqueous sodium chloride (200 ml), and extracted with ethyl acetate. The organic layer was dried over anhydrous magnesium sulfate, and the solvent was evaporated under reduced pressure. Subsequently, the resulting residue was purified by silica gel column chromatography (eluent: n-hexane/ethyl acetate=20/1), to afford the entitled compound N-(2-fluorophenyl)-2-methylthiopropionimidate methyl ester as pale yellow oil (7.84 g, 95%). The physico-chemical values are as follows.

$^1$H-NMR (CDCl$_3$) δ: 1.16 (6H, brs), 2.38 (3H, s), 2.81–2.96 (1H, m), 6.74–6.80 (1H, m), 6.95–7.09 (3H, m).

Production Example 1

3-Biphenyl-4-yl-4-(2-fluorophenyl)-5-isopropyl-4H-1,2,4-triazole

N-(2-Fluorophenyl)-2-methylthiopropionimidate methyl ester (7.84 g) prepared in the Reference Example 1 and biphenyl-4-carboxylic acid hydrazide (5.25 g) were dissolved in N,N-dimethylformamide (50 ml), followed by addition of p-toluenesulfonic acid·monohydrate (941 mg), and stirred at 120° C. for 59 hours. After the reaction solution was cooled to ambient temperature, the resulting solution was concentrated under reduced pressure. The resulting residue was purified by silica gel column chromatography (eluent: chloroform-chloroform/methanol=100/1 to 50/1 to 20/1), to afford 3-biphenyl-4-yl-4-(2-fluorophenyl)-5-isopropyl-4H-1,2,4-triazole as pale yellow solid (5.98g, 68%). A part of the product was recrystallized from ethyl acetate, to afford the entitled compound as pale yellow crystal. The physico-chemical values are as follows.

mp: 201–204° C. $^1$H-NMR (DMSO-d$_6$) δ: 1.15 (3H, d, J=6.8 Hz), 1.28 (3H, d, J=6.8 Hz), 2.72–2.82 (1H, m), 7.36–7.54 (7H, m), 7.66–7.71 (5H, m), 7.83 (1H, ddd, J=1.4 Hz, 7.8 Hz, 7.8 Hz).

Reference Example 2

N-(2-Bromophenyl)-6-phenylthionicotinimidate ethyl ester (1) 6-Phenylnicotinic acid (10.1 g) was dissolved in dimethylformamide (100 ml), followed by addition of 1-hydroxybenzotriazole (7.54 g), 1-ethyl-3-(3-dimethylaminopropyl)carbodiimide hydrochloride salt(10.7 g) and 2-bromoaniline (8.72 g), and stirred at ambient temperature for 13 hours, at 60° C. for 4 hours and at 100° C. for 2 hours. After the reaction solution was cooled to ambient temperature, the resulting solution was concentrated under reduced pressure, followed by addition of water and chloroform. The organic layer was separated, washed sequentially in water, saturated aqueous sodium hydrogen carbonate solution and water, and dried over anhydrous magnesium sulfate. After the solvent was evaporated under reduced pressure, the resulting residue was washed with a mixture solvent of n-hexane and diisopropyl ether, to afford N-(2-bromophenyl)-6-phenylnicotinamide as white solid (11.3 g, 63%). The physico-chemical values are as follows.

$^1$H-NMR (DMSO-d$_6$) δ: 7.23–7.31 (1H, m), 7.42–7.63 (5H, m), 7.75 (1H, dd, J=1.0, 7.8 Hz), 8.13–8.23 (3H, m), 8.42 (1H, dd, J=2.4, 8.3 Hz), 9.24 (1H, dd, J=2.0 Hz), 10.32 (1H, s).

(2) N-(2-Bromophenyl)-6-phenylnicotinamide (11.3 g) was dissolved in toluene (200 ml), followed by addition of the Lawesson reagent (7.12 g), and refluxed under heating for 3 hours. The resulting residue was purified by silica gel column chromatography (eluent: toluene-toluene/acetone=20/1), to afford an oily product. Subsequently, the oily product was dissolved in ethanol (70 ml), followed by addition of aqueous 0.5 mol/liter sodium hydroxide solution (130 ml) and methyl iodide(3.0 ml), and stirred at ambient temperature for 2 hours. After ethyl acetate was added to the reaction solution to separate the organic layer, the organic layer was washed with saturated aqueous sodium chloride and dried over anhydrous magnesium sulfate. After the solvent was evaporated under reduced pressure, the resulting residue was purified by silica gel column chromatography (developing solvent: n-hexane/ethyl acetate=10/1), to affordr the entitled compound N-(2-bromophenyl)-6-phenylthionicotinimidate methyl ester as yellow oil (8.46 g, 69%). The physico-chemical values are as follows.

$^1$H-NMR (DMSO-d$_6$) δ: 2.85 (3H, brs), 6.60–8.20 (11H, m), 8.52 (1H, brs).

Production Example 2

5-[4-(2-Bromophenyl)-4H-1,2,4-triazol-3-yl]-2-phenylpyridine

N-(2-Bromophenyl)-6-phenylthionicotinimidate methyl ester (8.46 g) prepared in the Reference Example 2 was dissolved in N,N-dimethylformamide (20 ml), followed by addition of formyl hydrazide (2.65 g) and p-toluenesulfonic acid·monohydrate (420 mg), and stirred at 140° C. for 23 hours. After the reaction solution was cooled to ambient temperature, saturated aqueous sodium hydrogen carbonate solution was added to the resulting solution, and extracted with chloroform. The extract was dried over anhydrous magnesium sulfate. After the solvent was evaporated under reduced pressure, the resulting residue was purified by silica gel column chromatography (eluent: chloroform/methanol=100/1), to afford the entitled compound as yellow solid (8.34 g, quantitative). The physico-chemical values are as follows.

FAB-MS m/z: 377 (M$^+$+H). $^1$H-NMR (DMSO-d$_6$) δ: 7.30–7.69 (5H, m), 7.79–7.91 (3H, m), 8.00–8.12 (3H, m), 8.66 (1H, brd, J=2.1 Hz), 8.96 (1H, s).

Production Example 3

5-[5-Bromo-4-(2-bromophenyl)-4H-1,2,4-triazol-3-yl]-2-phenylpyridine

5-[4-(2-Bromophenyl)-4H-1,2,4-triazol-3-yl]-2-phenylpyridine prepared in the Production Example 2 was dissolved in a mixture solvent of carbon tetrachloride (100 ml) and acetic acid (100 ml), followed by addition of n-bromosuccinimide (5.90 g), and refluxed under heating for 3 hours. After the reaction solution was cooled to ambient temperature, the solution was concentrated-under reduced pressure. Saturated aqueous sodium hydrogen carbonate solution was added to the resulting residue, and extracted with chloroform. Subsequently, the organic layer was dried over anhydrous magnesium sulfate. After the solvent was evaporated under reduced pressure, the resulting residue was purified by silica gel column chromatography (eluent: n-hexane/ethyl acetate=3/1), to afford the entitled compound as yellow solid (6.96 g, 69%). The physico-chemical values are as follows.

FAB-MS m/z: 454 (M$^+$+H). $^1$H-NMR (DMSO-d$_6$) δ: 7.43–7.52 (3H, m), 7.62 (1H, ddd, J=2.0, 7.8, 7.8 Hz), 7.71 (1H, ddd, J=1.5, 7.8, 7.8 Hz), 7.83 (1H, dd, J=2.5, 8.3 Hz), 7.92–7.98 (2H, m), 8.05 (1H, dd, J=1.0, 8.3 Hz), 8.06–8.11 (2H, m), 8.67 (1H, dd, J=1.0, 2.5 Hz).

Reference Example 3

N-(2,1,3-Benzooxadiazol-4-yl)-6-phenylthionicotinimidate methyl ester

In the same manner as in the Reference Example 1, the entitled compound as yellow oil was obtained from 2,1,3- benzooxadiazol-4-ylamine and 6-phenylnicotinoyl chloride. The physico-chemical values are as follows.

$^1$H-NMR (CDCl$_3$) δ: 2.60 (3H, s), 6.53–6.55 (1H, m), 7.20–7.96 (9H, m), 8.65–8.72 (1H, m).

Production Example 4

4-[3-(6-Phenylpyridin-3-yl)-4H-1,2,4-triazol-4-yl]-2,1,3-benzooxadiazole

In the same manner as in the Production Example 2, the entitled compound as yellow solid was obtained (2.80 g, 96%) from N-(2,1,3-benzooxadiazol-4-yl)-6-phenylthionicotinimidate methyl ester (2.96 g) prepared in the Reference Example 3. The physico-chemical values are as follows.

FAB-MS m/z: 341 (M$^+$+H). $^1$H-NMR (DMSO-d$_6$) δ: 7.45–7.53 (3H, m), 7.78 (1H, m), 7.88 (1H, d, J=7.0 Hz), 7.91–8.05 (4H, m), 8.26 (1H, d, J=9.0 Hz), 8.81 (1H, m), 9.15 (1H, s).

Production Example 5

4-[3-Bromo-5-(6-phenylpyridin-3-yl)-4H-1,2,4-triazol-4-yl]-2,1,3-benzooxadiazole In the same manner as in the Production Example 3, the entitled compound as yellow solid was obtained (1.01 g, 46%) from 4-[3-(6-phenylpyridin-3-yl)-4H-1,2,4-triazol-4-yl]-2,1,3-benzooxadiazole (1.80 g) recovered in the Production Example 4. The physico-chemical values are as follows.

FAB-MS m/z: 419 (M$^+$+H). $^1$H-NMR (DMSO-d$_6$) δ: 7.45–7.53 (3H, m), 7.85–7.91 (2H, m), 7.95 (1H, d, J=8.3 Hz), 8.03–8.08 (2H, m), 8.18 (1H, d, J=6.9 Hz), 8.41 (1H, d, J=9.3 Hz), 8.76 (1H, d, J=1.9 Hz).

In the same manner, compounds shown in Table (1) were synthetically prepared.

In the table, the abbreviations represent the following.
Pr.Ex.: Production Example No.
Ph: phenyl
Pyr: pyridyl
Me: methyl
Et: ethyl
iPr: isopropyl
cPr: cyclopropyl
cHex: cyclohexyl
Ac: acetyl
Bz: benzoyl
Py: pyridyl
Qin: quinolyl
Im: imidazolyl.

Herein, the substituting position of a substituent capable of substituting plural positions is expressed before the substituent (ex. 6-Br). Additionally, the binding position of hetero ring is expressed before the hetero ring (ex. 4-Py, 2-Qin).

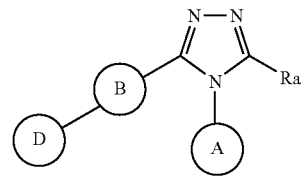

(1)

| PrEx. | Ra | Ring A | Substituent on UZ,13/24 ring A | | Ring B | Substituent on ring B | Ring D | Substituent on ring D | DATA: MS m/z |
|---|---|---|---|---|---|---|---|---|---|
| 6 | Me | Ph | 2-OMe | | Ph | H | 2-thiophen | H | M$^+$ + H: 348 (ESI) |
| 7 | Me | Ph | 2-OMe | | Ph | H | 2-benzofuran | H | M$^+$ + H: 382 (ESI) |
| 8 | Me | Ph | 2-F | — | Ph | H | Ph | H | M$^+$ + H: 330 (FAB) |
| 9 | Et | Ph | 2-F | — | Ph | H | Ph | H | M$^+$ + H: 344 (FAB) |
| 10 | Me | Ph | 2-NH$_2$ | — | Ph | H | Ph | H | M$^+$ + H: 327 (FAB) |
| 11 | Me | Ph | 1H-Im-1-yl | — | Ph | H | Ph | H | M$^+$ + H: 378 (FAB) |
| 12 | Me(CH$_2$)$_2$— | Ph | 2-F | — | Ph | H | Ph | H | M$^+$+ H: 358 (FAB) |
| 13 | Me(CH$_2$)$_3$— | Ph | 2-F | — | Ph | H | Ph | H | M$^+$+ H: 372 (FAB) |
| 14 | Me(CH$_2$)$_4$— | Ph | 2-F | — | Ph | H | Ph | H | M$^+$+ H: 386 (FAB) |
| 15 | Me(CH$_2$)$_5$— | Ph | 2-F | — | Ph | H | Ph | H | M$^+$+ H: 400 (FAB) |
| 16 | Me$_2$CHCH$_2$— | Ph | 2-F | — | Ph | H | Ph | H | M$^+$+ H: 372 (FAB) |
| 17 | Me | Ph | 2-OMe | 6-Me | Ph | H | Ph | H | M$^+$ + H: 356 (FAB) |
| 18 | Me | Ph | 5-NO$_2$ | 2-OMe | Ph | H | Ph | H | M$^+$ + H: 387 (FAB) |
| 19 | Me | Ph | 5-CF$_3$ | 2-OMe | Ph | H | Ph | H | M$^+$ + H: 410 (FAB) |
| 20 | Me | Ph | 4-F | — | Ph | H | Ph | H | M$^+$ + H: 330 (FAB) |
| 21 | Et | Ph | 2-F | 6-F | Ph | H | Ph | H | M$^+$ + H: 362 (FAB) |
| 22 | Et | Ph | 2-F | 3-F | Ph | H | Ph | H | M$^+$ + H: 362 (FAB) |
| 23 | Et | Ph | 2-Cl | 6-Cl | Ph | H | Ph | H | M$^+$ + H: 394 (FAB) |
| 24 | Et | Ph | 2-Cl | 3-Cl | Ph | H | Ph | H | M$^+$ + H: 394 (FAB) |
| 25 | Et | Ph | 2-Me | — | Ph | H | Ph | H | M$^+$ + H: 340 (FAB) |
| 26 | Me | Ph | 2-NHMe | — | Ph | H | Ph | H | M$^+$ + H: 341 (FAB) |
| 27 | Me | Ph | 2-OMe | — | Ph | H | Ph | 3,5-di-Cl | M$^+$ : 410 (ESI) |
| 28 | Me$_2$CH— | Ph | H | — | Ph | H | Ph | H | M$^+$ + H: 340 (FAB) |
| 29 | Me$_3$C— | Ph | 2-F | — | Ph | H | Ph | H | M$^+$ + H: 372 (FAB) |
| 30 | Br— | Ph | 2-F | — | Ph | H | Ph | H | M$^+$ + H: 395 (FAB) |
| 31 | Me | Ph | 2-Et | — | Ph | H | Ph | H | M$^+$ + H: 340 (FAB) |
| 32 | Me | Ph | 2-Me(CH$_2$) | — | Ph | H | Ph | H | M$^+$ + H: 354 (FAB) |

-continued

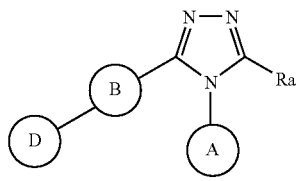

(1)

| PrEx. | Ra | Ring A | Substituent on UZ,13/24 ring A | Ring B | Substituent on ring B | Ring D | Substituent on ring D | DATA: MS m/z |
|---|---|---|---|---|---|---|---|---|
| 33 | Et | Ph | 2-OH | — | Ph | H | Ph | H | M+ + H: 342 (FAB) |
| 34 | Me | Ph | 2-F | — | Ph | H | Ph | 3,5-di-CF₃ | M+ + H: 466 (FAB) |
| 35 | Me | Ph | 3-F | — | Ph | H | Ph | H | M+ + H: 330 (FAB) |
| 36 | Me | Ph | 3-CF₃ | — | Ph | H | Ph | 3,5-di-CF₃ | M+ + H: 516 (FAB) |
| 37 | Et | Ph | 3-CF₃ | 2-F | Ph | H | Ph | H | M+ + H: 412 (FAB) |
| 38 | Et | Ph | 2-Me | 3-CF₃ | Ph | H | Ph | H | M+ + H: 408 (FAB) |
| 39 | Et | Ph | 2-Me | 3-Me | Ph | H | Ph | H | M+ + H: 354 (FAB) |
| 40 | Et | Ph | 2-Me | 3-F | Ph | H | Ph | H | M+ + H: 358 (FAB) |
| 41 | Et | Ph | 2-Me | 3-Cl | Ph | H | Ph | H | M+ + H: 374 (FAB) |
| 42 | Et | Ph | 2-Me | 3-Br | Ph | H | Ph | H | M+ + H: 418 (FAB) |
| 43 | Et | Ph | 2-Me | 3-NH₂ | Ph | H | Ph | H | M+ + H: 355 (FAB) |
| 44 | Et | Ph | 2-Me | 3-NMe₂ | Ph | H | Ph | H | M+ + H: 383 (FAB) |
| 45 | Et | Ph | 2-Me | 3-OH | Ph | H | Ph | H | M+ + H: 356 (FAB) |
| 46 | Et | Ph | 2-Me | 3-OMe | Ph | H | Ph | H | M+ + H: 370 (FAB) |
| 47 | Et | Ph | 2-Me | 3-Cn | Ph | H | Ph | H | M+ + H: 365 (FAB) |
| 48 | Et | Ph | 3-C≡CH | 2-Me | Ph | H | Ph | H | M+ + H: 364 (FAB) |
| 49 | Et | Ph | 2-Me | 3-NO₂ | Ph | H | Ph | H | M+ + H: 385 (FAB) |
| 50 | Et | Ph | 2-Cl | 3-CN | Ph | H | Ph | H | M+ + H: 385 (FAB) |
| 51 | Et | Ph | 2-F | 3-CN | Ph | H | Ph | H | M+ + H: 369 (FAB) |
| 52 | Et | Ph | 2-OH | 3-CN | Ph | H | Ph | H | M+ + H: 367 (FAB) |
| 53 | Et- | Ph | 2-F | — | Ph | 2-Cl | Ph | H | M+ + H: 378 (FAB) |
| 54 | Et- | Ph | 2-F | — | Ph | 3-Cl | Ph | H | M+ + H: 378 (FAB) |

Reference Example 4

N-(2,6-Difluorophenyl)-2-methylthiopropionimidate methyl ester

In the same manner as in the Reference Example 1, the entitled compound as colorless oil was obtained from 2,6-difluoroaniline. The physico-chemical values are as follows.
FAB-MS m/z: 230 (M⁺+H).

Example 1

5-[4-(2,6-Difluorophenyl)-5-isopropyl-4H-triazol-3-yl]-2-phenylpyridine

In the same manner as in the Production Example 1, the entitled compound as white crystal (recrystallized from ethyl acetate) was obtained (467 mg, 35%) from N-(2,6-difluorophenyl)-2-methylthiopropionimidate methyl ester (2.32 g) prepared in the Reference Example 4 and 6-phenylnicitinic acid hydrazide (750 mg). The physico-chemical values are as follows.
mp: 183–185° C. ¹H-NMR (DMSO-d₆) δ: 1.24 (6H, d, J=8 Hz), 2.76–2.85 (1H, m), 7.44–7.56 (5H, m), 7.76–7.85 (2H, m), 8.05 (1H, dd, J=8.3 Hz), 8.06–8.12 (2H, m), 8.64 (1H, d, J=1.9 Hz).

Reference Example 5

N-(2,1,3-Benzooxodiazol-4-yl)-2-methylthiopropionimidate methyl ester

In the same manner as in the Reference Example 1, the entitled compound was obtained as yellow oil from 2,1,3-benzooxadiazol-4-ylamine. The physico-chemical values are as follows.
¹H-NMR (CDCl₃) δ: 1.20 (6H, d, J=6.8 Hz), 2.91 (1H, m), 6.56 (1H, dd, J=0.6, 6.8 Hz), 7.35 (1H, dd, J=9.2, 6.9 Hz), 7.47 (1H, dd, J=0.7, 9.0 Hz).

Example 2

4-[3-Isopropyl 5-(6-phenylpyridin-3-yl)-4H-1,2,4-triazol-4-yl]-2,1,3-benzooxadiazole In the same manner as in the Production Example 1, the entitled compound as white crystal (recrystallized from a mixture solvent of n-hexane and toluene) was obtained (126 mg, 22%) from N-(2,1,3-benzooxadiazol-4-yl)-2-methylthiopropionimidate methyl ester (323 mg) prepared in the Reference Example 5 and 6-phenylnicotinic acid hydrazide (500 mg). The physico-chemical values are as follows.
mp: 107–108° C. ¹H-NMR (DMSO-d₆) δ: 1.12 (3H, d, J=6.9 Hz), 1.29 (3H, d, J=6.9 Hz), 2.86–2.98 (1H, m), 7.40–7.50 (3H, m), 7.78–7.86 (2H, m), 7.91 (1H, d, J=8.3 Hz), 8.01–8.05 (2H, m), 8.12 (1H, d, J=6.8 Hz), 8.34 (1H, d, J=8.8 Hz), 8.69 (1H, d, J=2.0 Hz).

Example 3

5-(3-Biphenyl-4-yl-5-ethyl-4H-1,2,4-triazol-4-yl) isoquinoline

A mixture of 2-biphenyl-4-yl-5-ethyl-1,3,4-oxodiazole (3.00 g), 5-aminoisoquinoline (3.00 g) and p-toluenesulfonic acid·monohydrate (0.65 g) was stirred at 150° C. for 3 hours, followed by addition of p-toluenesulfonic acid-monohydrate (0.65 g), and further stirred at 180° C. for 6 hours. The reaction mixture was cooled to ambient temperature, followed by addition of water and chloroform. Subsequently, potassium carbonate was added to the mixture, to adjust the mixture to basic. After the organic layer was separated, the aqueous layer was extracted with chloroform. The organic layers were combined together, washed with saturated aqueous sodium chloride, and dried over anhydrous magnesium sulfate. After the solvent was evaporated under reduced pressure, the resulting residue was purified by alumina column chromatography (eluent: chloroform) and subsequently by silica gel column chromatography (eluent: chloroform/methanol=20/1), and was then recrystallized from ethyl acetate, to afford the entitled compound as colorless needle crystal (1.45 g, 32%). The physico-chemical values are as follows.

mp: 228–230° C. $^1$H-NMR (CDCl$_3$) δ: 1.09 (3H, t, J=7.6 Hz), 2.33–2.50 (2H, m), 7.11 (1H, d, J=5.8 Hz), 7.31–7.42 (5H, m), 7.53–7.58 (4H, m), 7.89–7.91 (1H, t, J=7.9 Hz), 8.17 (1H, d, J=7.4 Hz), 8.42 (1H, d, J=8.3 Hz), 8.54 (1H, d, J=6.3 Hz), 9.51 (1H, s).

Reference Example 6

3-Amino-2-methylbenzamide

2-Methyl-3-nitrobenzamide (8.85 g) was dissolved in a mixture solvent of ethanol (300 ml) and tetrahydrofuran (200 ml), followed by addition of 10% palladium-carbon (800 mg). The resulting mixture was stirred under hydrogen atmosphere at ambient temperature and atmospheric pressure for 6 hours. After insoluble materials were filtered off, the filtrate was concentrated under reduced pressure and washed with isopropyl ether, to afford the entitled compound as white solid (6.73 g, 91%). The physico-chemical values are as follows.

$^1$H-NMR (DMSO-d$_6$) δ: 2.04 (3H, s), 4.91(2H, s), 6.51 (1H, dd J=1.0 Hz, 7.5 Hz), 6.64 (1H, dd, J=1.0 Hz, 7.5 Hz), 6.88 (1H, dd, J=7.0 Hz, 7.5 Hz), 7.18 (1H, s), 7.51 (1H, s).

Reference Example 7

5-[5-(3-Methoxypropyl)-1,3,4-oxadiazol-2-yl]-2-phenylpyridine (1) Carbazic acid tert-butyl ester (9.21 g) was dissolved in pyridine (120 ml), followed by addition of 4-methoxybutyric acid (9.06 g) and 1-ethyl-3-(3-dimethylaminopropyl)carbodiimide hydrochloride salt (20.0 g), and stirred at ambient temperature for 64 hours. After the reaction solution was concentrated under reduced pressure, ethyl acetate was added to the residue, which was then washed with aqueous 1 mol/liter hydrochloric acid solution, saturated aqueous sodium hydrogen carbonate solution and saturated aqueous sodium chloride, and dried over anhydrous sodium sulfate. After the solvent was evaporated under reduced pressure, N'-(4-methoxybutyryl)hydrazine carboxylic acid tert-butyl ester was obtained in yellow oil (9.30 g, 57%). The physico-chemical values are as follows.

$^1$H-NMR (DMSO-d$_6$) δ: 1.39 (9H, s), 1.65–1.78 (2H, m), 2.07–2.12 (2H, m), 3.21 (3H, s), 3.30–3.34 (2H, m), 8.64 (1H, s), 9.46 (1H, s).

(2) N'-(4-Methoxybutyryl)hydrazine carboxylic acd tert-butyl ester (9.30 g) was dissolved in ethyl acetate (50 ml), followed by addition of 4 mol/liter hydrochloric acid/ethyl acetate solution (150 ml), and stirred at ambient temperature for 2 hours. After the reaction solution was concentrated under reduced pressure, the resulting residue was washed with n-hexane, to afford 4-methoxybutyric acid hydrazide hydrochloride salt as pale yellow solid (5.99 g, 89%). The physico-chemical values are as follows.

$^1$H-NMR (DMSO-d$_6$) δ: 1.71–1.80 (2H, m), 2.27 (2H, t, J=7.5 Hz), 3.22 (3H, s), 3.31 (2H, t, J=6.3 Hz), 10.43 (3H, brs), 11.04 (1H, s).

(3) 6-Phenylnicotinic acid (5.90 g) was dissolved in pyridine (150 ml), followed by addition of 4-methoxybutyric acid hydrazide hydrochloride salt (5.99 g) and 1-ethyl-3-(3-dimethylaminopropyl)carbodiimide hydrochloride salt (8.51 g), and stirred at 60° C. for 10 hours. After the reaction solution was cooled to ambient temperature, the solvent was evaporated under reduced pressure. The resulting residue was washed with water, to afford 6-phenylnicotinic acid N'-(4-methoxybutyryl)hydrazide as pale yellow solid (6.06 g, 65%). The physico-chemical values are as follows.

$^1$H-NMR (DMSO-d$_6$) δ: 1.75–1.84 (2H, m), 2.26 (2H, t, J=7.4 Hz), 3.25 (3H, s), 3.37 (2H, t, J=6.4 Hz), 7.43–7.57 (3H, m), 8.11–8.19 (3H, m), 8.31 (1H, dd, J=2.7 Hz, 8.3 Hz), 9.10–9.12 (1H, m), 9.96 (1H, brs), 10.53 (1H, brs).

(4) To 6-phenylnicotinic acid N'-(4-methoxybutyryl)hydrazide (6.06 g) was added phosphorus oxychloride (100 ml), and stirred at 100° C. for 3 hours. After the reaction solution was cooled to ambient temperature, the solution was concentrated under reduced pressure. To the resulting residue was added aqueous 1 mol/liter sodium hydroxide solution under ice cooling, and extracted with chloroform. After the organic layer was dried over anhydrous sodium sulfate, the solvent was evaporated under reduced pressure. The residue was purified by silica gel column chromatography (eluent: n-hexane/ethyl acetate=3/1 to 1/1 to 1/2 to 1/5), and washed with a mixture solvent of n-hexane and ethyl acetate, to afford the entitled compound 5-[5-(3-methoxypropyl)-1,3,4-oxadiazol-2-yl]-2-phenylpyridine 3.72 g, 65%). The physico-chemicalvalues are as follows.

$^1$H-NMR (DMSO-d$_6$) δ: 2.01–2.10 (2H, m), 3.02 (2H, t, J=7.4 Hz), 3.28 (3H, s), 3.47 (2H, t, J=6.0 Hz), 7.46–7.56 (3H, m), 8.13–8.22 (3H, m), 8.40 (1H, dd, J=2.2 Hz, 8.4 Hz), 9.22–9.23 (1H, m).

Example 4

3-[3-(3-Methoxypropyl)-5-(6-phenylpyridin-3-yl)-4H-1,2,4-triazol-4-yl]-2-methylbenzamide 5-[5-(3-Methoxypropyl)-1,3,4-oxadiazol-2-yl]-2-phenylpyridine (1.0 g) prepared in the Reference Example 7 was dissolved in 1,3-dimethyl-2-imidazolidinone (10 ml), followed by addition of 3-amino-2-methylbenzamide (1.53 g) prepared in the Reference Example 6 and D-10-camphorsulfonic acid (290 mg), and stirred at 200° C. for 16 hours. After the reaction solution was cooled to ambient temperature, chloroform was added to the solution, which was then washed with saturated aqueous sodium hydrogen carbonate solution. The organic layer was dried over anhydrous magnesium sulfate, and the solvent was evaporated under reduced pressure. The resulting residue was purified by silica gel column chromatography (eluent: chloroform/methanol=10/1), to afford the entitled compound (812 mg, 56%). The physico-chemical values are as follows.

FAB-MS m/z: 428 (M$^+$+H). $^1$H-NMR (DMSO-d$_6$) δ: 1.86–1.93 (2H, m), 1.89 (3H, s), 2.46–2.54 (2H, m), 3.17 (3H, s), 3.34–3.37 (2H, m), 7.43–7.53 (4H, m), 7.58–7.62

(2H, m), 7.67 (1H, brd, J=7.3 Hz), 7.83 (1H, dd, J=2.4 Hz, 8.3 Hz), 7.96–8.00 (2H, m), 8.06–8.09 (2H, m), 8.60 (1H, d, J=2.4 Hz).

Example 5

3-[3-(3-Methoxypropyl)-5-(6-phenylpyridin-3-yl)-4H-1,2,4-triazol-4-yl]-2-methylbenzonitrile Phosphorus oxychloride (8 ml) was added to 3-[3-(3-methoxypropyl)-5-(6-phenylpyridin-3-yl)-1,2,4-triazol-4-yl]-2-methylbenzamide (770 mg) prepared in the Example 4, and refluxed under heating for 3 hours. After the reaction solution was cooled to ambient temperature, the solution was concentrated under reduced pressure. Chloroform was added to the resulting residue, which was then washed with saturated aqueous sodium hydrogen carbonate solution. Subsequently, the organic layer was dried over anhydrous magnesium sulfate. After the solvent was evaporated under reduced pressure, the resulting solid was recrystallized from ethyl acetate, to afford the entitled compound as white crystal (386 mg, 52%). The physico-chemical values are as follows.

mp: 144–145° C. $^1$H-NMR (DMSO-$d_6$) δ: 1.84–1.92 (2H, m), 2.08 (3H, s), 2.45–2.61 (2H, m), 3.17 (3H, s), 3.35 (2H, t, J=6.4 Hz), 7.43–7.52 (3H, m), 7.68 (1H, t, J=7.8 Hz), 7.77 (1H, dd, J=8.3, 1.9 Hz), 7.97–8.02 (2H, m), 8.06–8.12 (3H, m), 8.64 (1H, d, J=2.5 Hz).

Reference Example 8

5-(5-Ethyl-1,3,4-oxadiazol-2-yl)-2-phenylpyridine

In the same manner as in the Reference Example 7, the entitled compound was obtained as pale yellow solid from propionic acid. The physico-chemical values are as follows.
$^1$H-NMR (DMSO-$d_6$) δ: 1.37 (3H, t, J=7.6 Hz), 2.99 (2H, q, J=7.6 Hz), 7.43–7.58 (3H, m), 8.16–8.21 (3H, m), 8.41 (1H, dd, J=2.2 Hz, 8.4 Hz), 9.22–9.24 (1H, m).

Example 6

3-[3-Ethyl-5-(6-phenylpyridin-3-yl)-4H-1,2,4-triazol-4-yl]-2-methylbenzonitrile

In the same manner as in Example 4, 3-[3-ethyl-5-(6-phenylpyridin-3-yl)-4H-1,2,4-triazol-4-yl]-2-methylbenzamide as yellow solid (550 mg, 57%) was obtained from 5-ethyl-1,3,4-oxadiazol-2-yl)-2-phenylpyridine (630 mg) prepared in the Reference Example 8 and 3-amino-2-methylbenzamide (1.13 g) prepared in the Reference Example 6.

Subsequently, the entitled compound as white crystal was obtained (242 mg, 46%) from 3-[3-ethyl-5-(6-phenylpyridin-3-yl)-4H-1,2,4-triazol-4-yl]-2-methylbenzamide (550 mg). The physico-chemical values are as follows.

mp: 162–163° C. $^1$H-NMR (DMSO-$d_6$) δ: 1.19 (3H, t, J=7.5 Hz), 2.08 (3H, s), 2.41–2.59 (2H, m), 7.43–7.52 (3H, m), 7.67 (1H, dd, J=7.8, 8.3 Hz), 7.76 (1H, dd, J=2.5, 8.3 Hz), 7.98–8.02 (2H, m), 8.05–8.12 (3H, m), 8.64 (1H, d, J=2.5 Hz).

Example 7

[4-(2-Bromophenyl)-5-(6-phenylpyridin-3-yl)-4H-1,2,4-triazol-3-yl]-N-(2-methoxyethyl)-N-methylamine In a sealed tube, N-(2-methoxyethyl)methylamine (3 ml) was added to 5-[5-bromo-4-(2-bromophenyl)-4H-1,2,4-triazol-3-yl]-2-phenylpyridine (1.0 g) prepared in the Production Example 3, and stirred at 180° C. for 13 hours and at 200° C. for 24 hours. After the reaction solution was cooled to ambient temperature, chloroform was added to the solution, which was then washed with saturated aqueous sodium hydrogen carbonate solution. The organic layer was dried over anhydrous magnesium sulfate. After the solvent was evaporated under reduced pressure, the resulting residue was washed with ethyl acetate, to afford the entitled compound as white solid (711 mg, 70%). The physico-chemical values are as follows.

FAB-MS m/z: 464 (M$^+$+H). $^1$H-NMR (DMSO-$d_6$) δ: 2.77 (3H, s), 3.15 (3H, s), 3.15–3.31 (4H, m), 7.43–7.52 (4H, m), 7.65 (1H, t, J=7.8 Hz), 7.73 (1H, dd, J=2.0, 8.3 Hz), 7.85 (1H, d, J=8.3 Hz), 7.96–7.98 (2H, m), 8.04–8.07 (2H, m), 8.56 (1H, d, J=2.4 Hz).

Example 8

2-{3-[N-(2-Methoxyethyl)-N-methylamino]-5-(6-phenylpyridin-3-yl)-4H-1,2,4-triazol-4-yl}benzonitrile

[4-(2-Bromophenyl)-5-(6-phenylpyridin-3-yl)-4H-1,2,4-triazol-3-yl]-N-(2-methoxyethyl)-N-methylamine (436 mg) prepared in the Example 7 was dissolved in N-methyl-2-pyrrolidone (5 ml), followed by addition of zinc cyanide (121 mg), calcium hydroxide (76 mg) and tetrakistriphenylphosphine palladium (326 mg), and stirred at 180° C. for 3 hours. After the reaction solution was cooled to ambient temperature, chloroform was added to the solution, from which insoluble materials were filtered off. The filtrate was washed with saturated aqueous sodium hydrogen carbonate solution, and the organic layer was dried over anhydrous magnesium sulfate. After the solvent was evaporated under reduced pressure, the resulting solid was recrystallized from ethyl acetate, to afford the entitled compound as white crystal (242 mg, 63%). The physico-chemical values are as follows.

mp: 148–149° C. $^1$H-NMR (DMSO-$d_6$) δ: 2.79 (3H, s), 3.11 (2H, t, J=5.8 Hz), 3.14 (3H, s), 3.25–3.33 (2H, m), 7.43–7.52 (3H, m), 7.72 (1H, dd, J=2.5 Hz, 8.8 Hz), 7.79 (1H, dt, J=1.0 Hz, 7.8 Hz), 7.96–8.02 (2H, m), 8.04–8.12 (4H, m), 8.56 (1H, d, J=2.0 Hz).

Example 9

4-(2,1,3-Benzooxadiazol-4-yl)-N-(2-methoxyethyl)-N-methyl-5-(6-phenylpyridin-3-yl)-4H-1,2,4-triazol-3-ylamine In a sealed tube, N-(2-methoxyethyl)methylamine (3 ml) and water (3 ml) were added to 4-[3-bromo-5-(6-phenylpyridin-3-yl)-4H-1,2,4-triazol-4-yl]-2,1,3-benzooxadiazol (336 mg) prepared in the Production Example 5, and stirred at 160° C. for 6 hours. After the reaction solution was cooled to ambient temperature, chloroform was added to the solution, which was then washed with saturated aqueous sodium hydrogen carbonate solution. The organic layer was dried over anhydrous magnesium sulfate. After the solvent was evaporated under reduced pressure, the resulting solid was recrystallized from ethyl acetate, to afford the entitled compound as white crystal (66 mg, 19%). The physico-chemical values are as follows.

mp: 133–134° C. $^1$H-NMR (DMSO-d$_6$) δ: 2.76 (3H, s), 3.00 (3H, s), 3.05–3.25 (4H, m), 7.40–7.50 (3H, m), 7.75–7.82 (2H, m), 7.90 (1H, d, J=8.8 Hz), 8.00–8.10 (3H, m), 8.30 (1H, d, J=9.3 Hz), 8.67 (1H, d, J=2.5 Hz).

Reference Example 9

N-(2-Fluorophenyl)thioacetoimidate methyl ester

In the same manner as in the Reference Example 1, the entitled compound was obtained in pale yellow oil from 2-fluoroaniline. The physico-chemical values are as follows.

$^1$H-NMR (CDCl$_3$) δ: 1.59 (3H, brs), 2.02 (3H, brs), 6.78–6.85 (1H, m), 6.98–7.11 (3H, m).

Reference Example 10

3-(4-Bromophenyl)-4-(2-fluorophenyl)-5-methyl-4H-1,2,4-triazole

In the same manner as in the Production Example 1, the entitled compound was obtained as white solid (810 mg, 89%) from N-(2-fluorophenyl)thioacetoimidate methyl ester (500 mg) prepared in the Reference Example 9 and 4-bromobezoic acid hydrazide (705 mg). The physico-chemical values are as follows.

FAB-MS m/z: 332 (M$^+$+H). $^1$H-NMR (DMSO-d$_6$) δ: 2.25 (3H, s), 7.28–7.75 (8H, m).

Example 10

4-(2-Fluorophenyl)-3-methyl-5-(4-thiophen-2-ylphenyl)-4H-1,2,4-triazole 3-(4-Bromophenyl)-4-(2-fluorophenyl)-5-methyl-4H-1,2,4-triazole (150 mg) prepared in the Reference Example 10 was dissolved in 1,2-dimethoxyethane (2 ml), followed by addition of tetrakis(triphenylphosphine)palladium (26 mg), and stirred at ambient temperature for 15 minutes. Subsequently, a solution of 2-thiophenboric acid (150 mg) in ethanol (0.5 ml) and aqueous 2 mol/liter sodium carbonate solution (0.45 ml) were added to the resulting mixture, and refluxed under heating for 4 hours. After the reaction solution was cooled to ambient temperature, insoluble materials were filtered off. To the resulting filtrate was added saturated aqueous sodium hydrogen carbonate solution, and extracted with ethyl acetate. The organic layer was dried over anhydrous magnesium sulfate, and the solvent was evaporated under reduced pressure. The resulting residue was purified by silica gel chromatography (eluent: chloroform/methanol=99/1 to 97/3) and recrystallized from ethanol, to afford the entitled compound as white solid (100 mg, 66%). The physico-chemical values are as follows.

FAB-MS m/z: 336 (M$^+$+H). $^1$H-NMR (DMSO-d$_6$) δ: 2.24 (3H, s), 7.12 (1H, dd, J=3.5, 4.5 Hz), 7.38–7.68 (10H, m).

Example 11

3-{4-[4-(2-Fluorophenyl)-5-methyl-4H-1,2,4-triazol-3-yl]phenyl}pyridine 3-(4-Bromophenyl)-4-(2-fluorophenyl)-5-methyl-4H-1,2,4-triazole (500 mg) prepared in the Reference Example 10 was dissolved in tetrahydrofuran (15 ml), followed by addition of n-butyl lithium (1.57 mol/liter hexane solution; 1.2 ml) at −78° C., and stirred at the same temperature for 20 minutes. Borate methyl ester (0.50 ml) was added to the mixture and stirred at ambient temperature for 3 hours. Under ice cooling, aqueous 2 mol/liter hydrochloric acid solution was added to adjust the solution to about pH 4, followed by extraction with chloroform. The organic layer was washed with saturated aqueous saline. The organic layer was dried over anhydrous magnesium sulfate, and the solvent was evaporated under reduced pressure, to afford a borate derivative as pale yellow oil (660 mg).

3-Bromopyridine (0.15 ml) was dissolved in 1,2-dimethoxyethane (5 ml), followed by addition of tetrakis (triphenylphosphine)palladium (87 mg), and stirred at ambient temperature for 15 minutes. To the reaction solution were added a solution of the borate derivative in ethanol (2 ml) and aqueous 2 mol/liter sodium carbonate solution (1.5 ml), and refluxed heating for 3 hours. After the reaction solution was cooled to ambient temperature, insoluble materials were filtered off, and the solvent was evaporated under reduced pressure. The resulting residue was purified by silica gel chromatography (eluent: chloroform/methanol=98/2) and washed with a mixture solvent of n-hexane and ethyl acetate, to afford the entitled compound as white solid (140 mg, 28%). The physico-chemical values are as follows.

FAB-MS m/z: 331 (M$^+$+H). $^1$H-NMR (DMSO-d$_6$) δ: 2.26 (3H, s), 7.44–7.56 (5H, m), 7.63–7.70 (1H, m), 7.74–7.79 (3H, m), 8.07–8.11 (1H, m), 8.56–8.60 (1H, m), 8.88–8.92 (1H, m).

Example 12

3-Biphenyl-4-yl-4-(2-fluorophenyl)-5-methylsulfanyl-4H-1,2,4-triazole (1) Biphenyl-4-carboxylic acid hydrazide (10.0 g) was dissolved in ethanol (250 ml), followed by addition of 2-fluorophenylisothiocyanate (5.8 ml), and stirred ambient temperature for 2 hours. The precipitate was filtered, to afford 1-(biphenyl-4-carbonyl)-4-(2-fluorophenyl)-thiosemicarbazide as white solid (12.3 g, 72%). The physico-chemical values are as follows.

FAB-MS m/z: 366 (M$^+$+H). $^1$H-NMR (DMSO-d$_6$) δ: 7.15–7.45 (5H, m), 7.50 (2H, t, J=7.5 Hz), 7.75 (2H, d, J=7.5 Hz), 7.82 (2H, d, J=8.5 Hz), 8.05 (2H, d, J=8.5 Hz), 9.64 (1H, s), 9.89 (1H, s), 10.66 (1H, s).

(2) 1-(Biphenyl-4-carbonyl)-4-(2-fluorophenyl)thiosemicarbazide (12.1 g) was suspended in aqueous 2 mol/liter sodium hydroxide solution (300 ml), and refluxed under heating for 3 hours. After the reaction solution was cooled to ambient temperature, the solution was neutralized under ice cooling with conc. hydrochloric acid. The precipitate was filtered and washed with water, to afford 5-biphenyl-4-yl-4-(2-fluorophenyl)-4H-1,2,4-triazole-3-thiol as pale yellow solid (11.2 g, 97%). The physico-chemical values are as follows.

FAB-MS m/z: 348 (M$^+$+H). $^1$H-NMR (DMSO-d$_6$) δ: 7.33–7.52 (8H, m), 7.53–7.70 (6H, m).

(3) 5-Biphenyl-4-yl-4-(2-fluorophenyl)-4H-1,2,4-triazole-3-thiol (2.7 g) was dissolved in acetonitrile (50 ml), followed by addition of methyl iodide (0.967 ml) and potassium carbonate (1.07 g), and stirred at ambient temperature for 3 hours. Water was added to the reaction solution, followed by extraction with chloroform. The organic layer was washed with saturated aqueous saline and dried over anhydrous magnesium sulfate. After the solvent was evaporated under reduced pressure, the resulting solid was recrystallized from a mixture solvent of acetonitrile and ethyl acetate, to afford the entitled compound 3-biphenyl- 4-yl-4-(2-fluorophenyl)-5-methylsulfanyl-4H-1,2,4-triazole as pale yellow crystal (2.03 g, 72%). The physico-chemical values are as follows.

mp: 199–200° C. $^1$H-NMR (DMSO-$d_6$) δ: 2.65 (3H, s), 7.35–7.56 (7H, m), 7.65–7.72 (5H, m), 7.77 (1H, dt, J=2.0, 7.8 Hz).

Example 13

3-Benzyloxymethyl-5-biphenyl-4-yl-4-(2-fluorophenyl)-4H-1,2,4-triazole (1) Biphenyl-4-carboxylic acid hydrazide (6.4 g) was dissolved in N,N-dimethylformamide (50 ml), followed by sequential addition of tetrahydrofuran (100 ml), benzyloxyacetic acid (5.0 g), 1-hydroxybenzotriazole (0.30 g) and 1-ethyl-3-(3-dimethylaminopropyl)carbodiimide hydrochloride salt (6.3 g), and stirred at ambient temperature for 2 hours. After the reaction solution was concentrated under reduced pressure, water was added to the resulting residue, and the precipitate was filtered. The precipitate was sequentially washed with aqueous 0.15 mol/liter hydrochloric acid solution and water, to afford biphenyl-4-carboxylic acid N'-(2-benzyloxyacetyl)hydrazide as pale yellow solid (10.8 g, quantitative). The physico-chemical values are as follows.

FAB-MS m/z: 361.

(2) To biphenyl-4-carboxylic acid N'-(2-benzyloxyacetyl)hydrazide (9.38 g) was added phosphorus oxychloride (30 ml), and stirred at 100° C. for one hour. After the reaction solution was cooled to ambient temperature, the reaction solution was concentrated under reduced pressure. To the resulting residue was added ethyl acetate, and the separated organic layer was washed with aqueous 1 mol/liter sodium hydroxide solution and dried over anhydrous magnesium sulfate, and the solvent was evaporated under reduced pressure to afford an oily product. Subsequently, 2-fluoroaniline (5 ml) and p-toluenesulfonic acid·monohydrate (200 mg) were added to the resulting oily product, and stirred at 140° C. for 4 hours. After the reaction solution was cooled to ambient temperature, ethyl acetate was added to the reaction solution. The separated organic layer was washed with aqueous 1 mol/liter sodium hydroxide solution and dried over anhydrous magnesium sulfate. The solvent was evaporated under reduced pressure. The resulting residue was purified by silica gel chromatography (eluent: n-hexane/ethyl acetate=3/1–1/1), to afford the entitled compound 3-benzyloxymethyl-5-biphenyl-4-yl-4-(2-fluorophenyl)-4H-1,2,4-triazole as pale yellow solid (6.60 g, 58%). The physico-chemical values are as follows.

FAB-MS m/z: 436 (M$^+$+H). $^1$H-NMR (DMSO-$d_6$) δ: 4.35 (1H, d, J=11.9 Hz), 4.40 (1H, d, J=11.9 Hz), 7.06–7.12 (2H, m), 7.23–7.52 (10H, m), 7.62–7.73 (5H, m), 7.81 (1H, ddd, J=1.7, 8.0, 9.5 Hz).

Example 14

[5-Biphenyl-4-yl-4-(2-fluorophenyl)-4H-1,2,4-triazol-3-yl]methanol

3-Benzyloxymethyl-5-biphenyl-4-yl-4-(2-fluorophenyl)-4H-1,2,4-triazole (6.00 g) was dissolved in chloroform (200 ml), followed by dropwise addition of 1 mol/liter boron trichloride-hexane solution (30 ml) at −44° C. and stirred at the same temperature for 30 minutes and at ambient temperature for one hour. To the reaction solution were added methanol (5 ml) and saturated aqueous sodium hydrogen carbonate solution (50 ml), followed by concentration under reduced pressure. To the resulting residue were added tetrahydrofuran (100 ml), aqueous 2 mol/liter sodium hydroxide solution (100 ml) and tetrabutylammoniumhydrogensulfate (0.10 g), and stirred at ambient temperature for 12 hours. The reaction solution was extracted with ethyl acetate, and the organic layer was dried over anhydrous magnesium sulfate. After the solvent was evaporated under reduced pressure, the resulting residue was purified by silica gel chromatography (eluent: chloroform/methanol=96/4) and recrystallized from a mixture solution of n-hexane-ethyl acetate-ethanol, to afford the entitled compound as white crystal (2.09 g, 44%). The physico-chemical values are as follows.

mp: 220–223° C. $^1$H-NMR (DMSO-$d_6$) δ: 4.47 (1H, dd, J=5.5, 13.2 Hz), 4.53 (1H, dd, J=5.5, 13.2 Hz), 5.46 (1H, t, J=5.5 Hz), 7.34–7.50 (7H, m), 7.59–7.75 (5H, m), 7.79 (1H, ddd, J=1.5, 8.2, 9.7 Hz).

Example 15

3-Biphenyl-4-yl-5-chloromethyl-4-(2-fluorophenyl)-4H-1,2,4-triazole

[5-Biphenyl-4-yl-4-(2-fluorophenyl)-4H-1,2,4-triazol-3-yl]methanol (1.81 g) was suspended in toluene (25 ml), followed by addition of thionyl chloride (1.5 ml) and chloroform (25 ml), and stirred at 60° C. for 5 hours. After the reaction solution was concentrated under reduced pressure, ethyl acetate was added to the reaction solution, which was washed with saturated aqueous sodium hydrogen carbonate solution. After the organic layer was dried over anhydrous magnesium sulfate, the solvent was evaporated under reduced pressure. The resulting white solid was washed with a mixture solution of n-hexane and ethyl acetate, to afford the entitled compound as white solid (1.54 g, 81%). The physico-chemical values are as follows.

FAB-MS m/z: 364 (M$^+$+H). $^1$H-NMR (DMSO-$d_6$) δ: 4.80 (1H, d, J=13.0 Hz), 4.87 (1H, d, J=13.0 Hz), 7.34–7.54 (7H, m), 7.66–7.75 (5H, m), 7.91 (1H, ddd, J=1.6, 6.2, 9.2 Hz).

Example 16

4-{[5-Biphenyl-4-yl-4-(2-fluorophenyl)-4H-1,2,4-triazol-3-yl]methyl}morpholine

Morpholine (0.599 ml) was dissolved in N,N-dimethylformamide (6 ml), followed by addition of sodium hydride (60%, 275 mg) under ice cooling, and stirred at the same temperature for 30 minutes. Under ice cooling, 3-biphenyl-4-yl-5-chloromethyl-4-(2-fluorophenyl)-4H-1,2,4-triazole (599 mg) was added to the reaction solution, and stirred at ambient temperature for 17 hours. After the reaction solution was concentrated under reduced pressure, saturated aqueous sodium hydrogen carbonate solution was added to the resulting residue, followed by extraction with chloroform. The organic layer was dried over anhydrous magnesium sulfate. The solvent was evaporated under reduced pressure, and the resulting residue was purified by silica gel chromatography (eluent: toluene/acetone=3/2 to 1/1), and recrystallized from a mixture solution of n-hexane and ethyl acetate, to afford the entitled compound as white crystal (211 mg, 74%). The physico-chemical values are as follows.

mp: 129–131° C. $^1$H-NMR (DMSO-$d_6$) δ: 2.13–2.26 (4H, m), 3.29–3.34 (4H, m), 3.50 (1H, d, J=14.2 Hz), 3.63 (1H, d, J=14.2 Hz), 7.36–7.51 (7H, m), 7.60–7.70 (5H, m), 7.81–7.85 (1H, m).

The following Tables (2) and (3) show the structural formulas and physico-chemical properties of the compounds of the Example.

In the tables, the abbreviation 'Ex' represents Example. Other abbreviations are as described above.

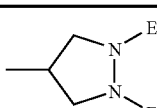

(2)

| Ex. | 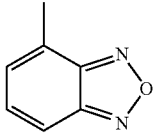 | A' | Ra | DATA: MS m/z |
|---|---|---|---|---|
| 17 | biphenyl-4-yl | 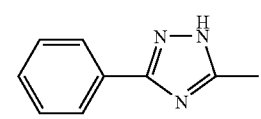 | Me | M+ + H: 362 (FAB) |
| 18 | biphenyl-4-yl | indan-2-yl | Et | M + H: 366 (FAB) |
| 19 | biphenyl-4-yl | cHex | Et | M+ + H: 332 (FAB) |
| 20 | biphenyl-4-yl | morpholin-4-yl | Me | M+ + H: 321 (FAB) |
| 21 | biphenyl-4-yl | 1H-pyrazol-3-yl | Me | M+ + H: 302 (FAB) |
| 22 | biphenyl-4-yl | 2-Ph-2H-pyrazol-3-yl | Et | M+ + H: 392 (FAB) |
| 23 | biphenyl-4-yl | 3-Me-pyridin-2-yl | Me | M+ + H: 327 (FAB) |
| 24 | biphenyl-4-yl | pyridin-3-yl | Me | M+ + H: 313 (FAB) |
| 25 | biphenyl-4-yl | 2-Cl-pyridin-3-yl | Me | M+ + H: 347 (FAB) |
| 26 | biphenyl-4-yl | 6-Cl-pyridin-3-yl | Me | M+ + H: 347 (FAB) |
| 27 | biphenyl-4-yl | 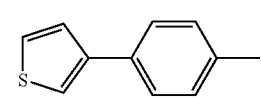 | Me | M+ + H: 354 (FAB) |
| 28 | biphenyl-4-yl | quinolin-8-yl | Et | M+ + H: 377 (FAB) |
| 29 | 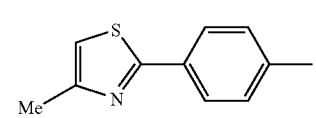 | 2-F-Ph | Me | M+ + H: 321 (FAB) |
| 30 | 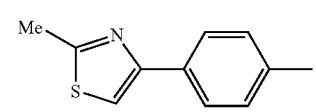 | 2-F-Ph | Me | M+ + H: 336 (FAB) |
| 31 | 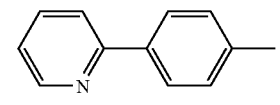 | 2-F-Ph | Me | M+ + H: 351 (FAB) |
| 32 | 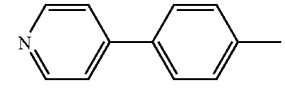 | 2-F-Ph | Me | M+ + H: 351 (FAB) |
| 33 |  | 2-F-Ph | Me | M+ + H: 331 (FAB) |
| 34 |  | 2-F-Ph | Me | M+ + H: 331 (FAB) |

-continued (2)

[Structure: triazole core with Rd-B', Re-D' chain, A' substituent, and Ra group]

[Sub-structure: D'(Re)-B'(Rd)- chain]

| Ex. | | A' | Ra | DATA: MS m/z |
|---|---|---|---|---|
| 35 | biphenyl-4-yl | 4-benzofurazanyl | Et | M+ + H: 368 (FAB) |
| 36 | biphenyl-4-yl | 4-benzofurazanyl | Me₂CH— | M+ + H: 382 (FAB) |
| 37 | biphenyl-4-yl | 4-benzothiadiazolyl | Et | M+ + H: 384 (FAB) |
| 38 | biphenyl-4-yl | 1-indanyl | Et | M+ + H: 366 (FAB) |
| 39 | biphenyl-4-yl | 5,6,7,8-tetrahydronaphthalen-1-yl | Et | M+ + H: 380 (FAB) |
| 40 | biphenyl-4-yl | 1-naphthyl | Et | M+ + H: 376 (FAB) |
| 41 | biphenyl-4-yl | 2-naphthyl | Et | M+ + H: 376 (FAB) |
| 42 | biphenyl-4-yl | 7-indolyl | Et | M+ + H: 365 (FAB) |

-continued (2)

[Structure: triazole core with Rd-B', Re-D', A', and Ra substituents]

| Ex. | Re-D'-B'- | A' | Ra | DATA: MS m/z |
|---|---|---|---|---|
| 43 | biphenyl-4-yl | 1-methylindol-7-yl (N-Me) | Et | M+ + H: 379 (FAB) |
| 44 | biphenyl-4-yl | 1H-benzimidazol-4-yl | Et | M+ + H: 366 (FAB) |
| 45 | biphenyl-4-yl | 1H-indazol-5-yl | Et | M+ + H: 366 (FAB) |
| 46 | biphenyl-4-yl | 1H-indazol-6-yl | Et | M+ + H: 366 (FAB) |
| 47 | biphenyl-4-yl | 1H-indazol-4-yl | Et | M+ + H: 366 (FAB) |
| 48 | biphenyl-4-yl | 1H-benzimidazol-7-yl | Et | M+ + H: 366 (FAB) |
| 49 | biphenyl-4-yl | 5,6,7,8-tetrahydroquinolin-8-yl | Et | M+ + H: 381 (FAB) |
| 50 | biphenyl-4-yl | 7-methylquinolin-8-yl | Et | M+ + H: 391 (FAB) |
| 51 | biphenyl-4-yl | 2-methylquinolin-8-yl | Et | M+ + H: 391 (FAB) |

-continued
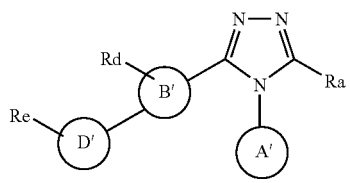
(2)
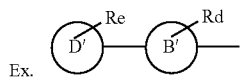
| Ex. | | A' | Ra | DATA: MS m/z |
|---|---|---|---|---|
| 52 | biphenyl-4-yl | 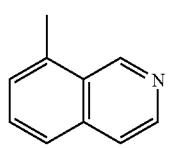 | Et | M⁺ + H: 377 (FAB) |
| 53 | biphenyl-4-yl | 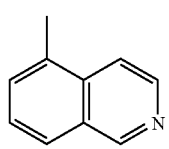 | Et | M⁺ + H: 377 (FAB) |
| 54 | biphenyl-4-yl | 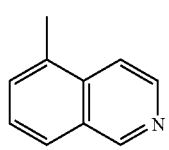 | Me(CH$_2$)$_2$— | M⁺ + H: 391 (FAB) |
| 55 | biphenyl-4-yl | 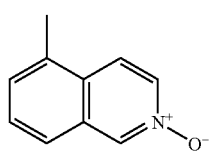 | MeO(CH$_2$)$_3$— | M⁺ + H: 421 (FAB) |
| 56 | biphenyl-4-yl | 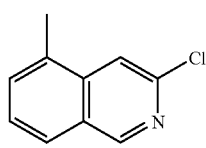 | Et | M⁺ + H: 393 (FAB) |
| 57 | biphenyl-4-yl | 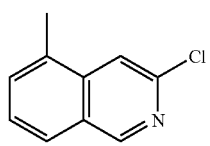 | Et | M⁺ + H: 411 (FAB) |
| 58 | biphenyl-4-yl | 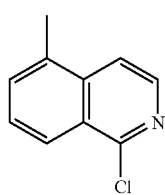 | Et | M⁺ + H: 411 (FAB) |

-continued (2)

| Ex. | D'-B'- (Re, Rd) | A' | Ra | DATA: MS m/z |
|---|---|---|---|---|
| 59 | biphenyl-4-yl | 5-methyl-8-chloroisoquinolin-yl | Et | M⁺ + H: 411 (FAB) |
| 60 | biphenyl-4-yl | 5-methyl-1-oxo-1,2-dihydroisoquinolin-yl | Et | M⁺ + H: 393 (FAB) |
| 61 | biphenyl-4-yl | 5-methyl-1,2,3,4-tetrahydroisoquinolin-yl | Et | M⁺ + H: 381 (FAB) |
| 62 | biphenyl-4-yl | 5-methyl-2-methyl-1,2,3,4-tetrahydroisoquinolin-yl | Et | M⁺ + H: 395 (FAB) |
| 63 | biphenyl-4-yl | 5-methylphthalazin-yl | Me₂CH— | M⁺ + H: 391 (FAB) |
| 64 | biphenyl-4-yl | 5-methylquinolin-yl | Et | M⁺ + H: 377 (FAB) |
| 65 | biphenyl-4-yl | | Et | M⁺ + H: 377 (FAB) |
| 66 | biphenyl-4-yl | 4-methylisoquinolin-yl | Et | M⁺ + H: 377 (FAB) |

-continued (2)

|     | Re—D'—B'—Rd | | | |
|-----|---|---|---|---|
| Ex. | D'-B' (Re, Rd) | A' | Ra | DATA: MS m/z |
| 67 | biphenyl-4-yl | 1-isoquinolinyl | Et | M⁺ + H: 377 (FAB) |
| 68 | phenyl-piperidin-4-yl (N-methyl) | 2-F-Ph | Et | M⁺ + H: 351 (FAB) |
| 69 | phenyl-tetrahydropyridin-4-yl (N-methyl) | 2-F-Ph | Et | M⁺ + H: 349 (FAB) |
| 70 | phenyl-piperidin-1-yl (4-methyl) | 2-F-Ph | Et | M⁺ + H: 351 (FAB) |
| 71 | phenyl-piperazin-1-yl (4-methyl) | 2-F-Ph | Et | M⁺ + H: 352 (FAB) |
| 72 | 6-phenylpyridin-3-yl | 2-F-Ph | Et | M⁺ + H: 345 (FAB) |
| 73 | 5-phenylpyridin-2-yl | 2-F-Ph | Et | M⁺ + H: 345 (FAB) |
| 74 | 6-phenylpyridin-3-yl | 2-F-Ph | Me₂CH— | M⁺ + H: 359 (FAB) |
| 75 | 6-phenylpyridin-3-yl | 2-F-Ph | MeO(CH₂)₃— | M⁺ + H: 389 (FAB) |
| 76 | 6-phenylpyridin-3-yl | 2-F-Ph | Me₂N— | M⁺ + H: 360 (FAB) |
| 77 | 6-phenylpyridin-3-yl | 2-F-Ph | EtNH— | M⁺ + H: 360 (FAB) |
| 78 | 6-phenylpyridin-3-yl N-oxide | 2-F-Ph | MeOCH₂CH₂NH— | M⁺ + H: 390 (FAB) |

-continued (2)

| Ex. | D'-B' (Re, Rd) | A' | Ra | DATA: MS m/z |
|---|---|---|---|---|
| 79 | Ph-pyridine | 2-F-Ph | MeO-CH2CH2-N(Me)- | M+ + H: 404 (FAB) |
| 80 | Ph-pyridine | 2-F-Ph | MeO-CH2CH2-N(Et)- | M+ + H: 418 (FAB) |
| 81 | Ph-pyridine | 2-F-Ph | MeO-CH2CH2-N(nPr)- | M+ + H: 432 (FAB) |
| 82 | Ph-pyridine | 2-F-Ph | tetrahydrofurfuryl-NH- | M+ + H: 416 (FAB) |
| 83 | Ph-pyridine | 2-F-Ph | (S)-tetrahydrofurfuryl-NH- | M+ + H: 416 (FAB) |
| 84 | Ph-pyridine | 2-F-Ph | (R)-tetrahydrofurfuryl-NH- | M+ + H: 416 (FAB) |
| 85 | Ph-pyridine N-oxide | 2-F-Ph | Et | M+ + H: 361 (FAB) |
| 86 | Ph-pyridine (3-Cl) | 2-F-Ph | Et | M+ + H: 379 (FAB) |
| 87 | Ph-pyridine (6-Cl) | 2-F-Ph | Et | M+ + H: 379 (FAB) |
| 88 | Ph-pyridine (4-NMe2) | 2-F-Ph | Et | M+ + H: 388 (FAB) |

-continued (2)

*[Structure: triazole core with substituents Rd-B', Re-D', A', Ra]*

| Ex. | Re-D'—B'-Rd | A' | Ra | DATA: MS m/z |
|---|---|---|---|---|
| 89 | 4-Ph, 2-phenylpyridin-5-yl | 2-F-Ph | Et | M⁺ + H: 421 (FAB) |
| 90 | 2-phenylpyridin-5-yl | 2-CN-Ph | Et | M⁺ + H: 352 (FAB) |
| 91 | 2-phenylpyridin-5-yl | 2-CN-Ph | Me₂CH— | M⁺ + H: 366 (FAB) |
| 92 | 2-phenylpyridin-5-yl | 2-CN-Ph | MeO(CH₂)₃— | M⁺ + H: 396 (FAB) |
| 93 | 2-phenylpyridin-5-yl | 2-CN-Ph | Me₂N- | M⁺ + H: 367 (FAB) |
| 94 | 2-phenylpyridin-5-yl | 2-CN-Ph | (tetrahydrofuran-2-yl)CH₂NH— | M⁺ + H: 437 (FAB) |
| 95 | 2-phenylpyridin-5-yl | 2-Cl-3-Me-6-CN-Ph | Et | M⁺ + H: 386 (FAB) |
| 96 | 2-phenylpyridin-5-yl | 2-Cl-3-Me-6-CN-Ph | Me₂CH— | M⁺ + H: 400 (FAB) |
| 97 | 2-phenylpyridin-5-yl | 2-Cl-3-Me-6-CN-Ph | MeO(CH₂)₃— | M⁺ + H: 430 (FAB) |
| 98 | 2-phenylpyridin-5-yl | 2,3-Me₂-6-CN-Ph | Me₂CH— | M⁺ + H: 380 (FAB) |

-continued
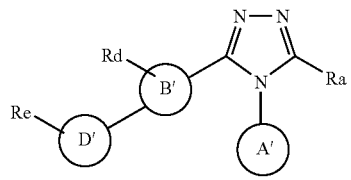
(2)
| Ex. | 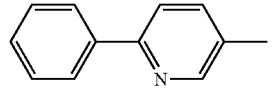 | A' | Ra | DATA: MS m/z |
|---|---|---|---|---|
| 99 | 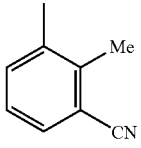 | 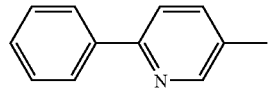 | EtNH— | M⁺ + H: 381 (FAB) |
| 100 | 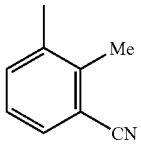 | 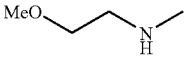 | 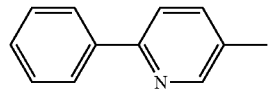 | M⁺ + H: 411 (FAB) |
| 101 | 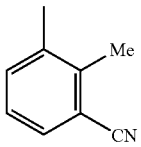 | 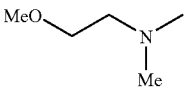 | 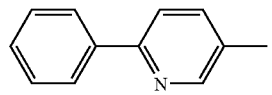 | M⁺ + H: 425 (FAB) |
| 102 | 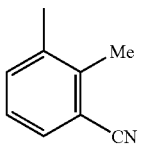 | 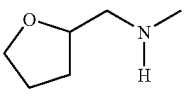 | 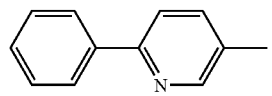 | M⁺ + H: 437 (FAB) |
| 103 | 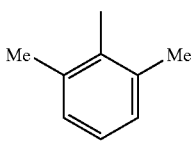 | 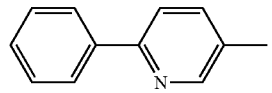 | Me₂CH— | M⁺ + H: 369 (ESI) |
| 104 | 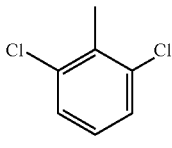 | 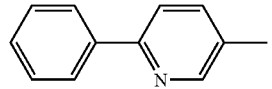 | Me₂CH— | M⁺ + H: 409 (ESI) |
| 105 | 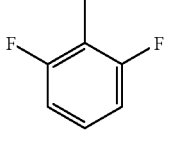 | 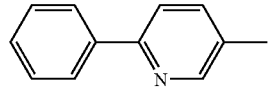 | MeO(CH₂)₃— | M⁺ + H: 407 (FAB) |
| 106 | 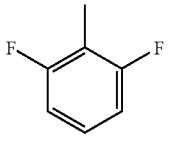 | 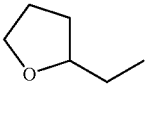 | | M⁺ + H: 419 (FAB) |

-continued (2)

| Ex. | D'—B'— (Re, Rd) | A' | Ra | DATA: MS m/z |
|---|---|---|---|---|
| 107 | phenyl-pyridine | 2,6-difluorophenyl | tetrahydropyran-4-ethyl (O ring with ethyl) | M+ + H: 433 (FAB) |
| 108 | phenyl-pyridine | 2,6-difluorophenyl | H2N— | M+ + H: 350 (FAB) |
| 109 | phenyl-pyridine | 2,6-difluorophenyl | CF3CH2— | M+ + H: 417 (FAB) |
| 110 | phenyl-pyridine | 2,6-difluorophenyl | CF3CF2— | M+ + H: 453 (FAB) |
| 111 | phenyl-pyridine | 2,6-difluorophenyl | CF3(CH2)2— | M+ + H: 431 (FAB) |
| 112 | tetrahydropyran-4-ethyl | 2,6-difluorophenyl | Me2CH— | M+ + H: 411 (FAB) |
| 113 | (2-fluorophenyl)-pyridine | 2,6-difluorophenyl | Me2CH— | M+ + H: 394 (FAB) |
| 114 | (4-fluorophenyl)-pyridine | 2,6-difluorophenyl | Me2CH— | M+ + H: 395 (FAB) |

-continued (2)

| Ex. | Re-D'-B'- (with Rd) | A' | Ra | DATA: MS m/z |
|---|---|---|---|---|
| 115 | 4-F-C6H4—pyridine—(2,6-difluoro-3-methylphenyl) | 2-methylphenyl | Me₂CH— | M⁺ + H: 395 (FAB) |
| 116 | phenyl—pyridine— | 4-methylbenzofurazan-4-yl | MeO(CH₂)₃— | M⁺ + H: 413 (FAB) |
| 117 | phenyl—pyridine— | 4-methylbenzofurazan-4-yl | Me₂N— | M⁺ + H: 384 (FAB) |
| 118 | phenyl—pyridine— | 5-methylisoquinolin-5-yl | Et | M⁺ + H: 378 (FAB) |
| 119 | phenyl—pyridine— | 5-methylisoquinolin-5-yl | Me(CH₂)₂— | M⁺ + H: 392 (FAB) |
| 120 | phenyl—pyridine— | 5-methylisoquinolin-5-yl | Me₂CH— | M⁺ + H: 392 (FAB) |
| 121 | phenyl—pyridine— | 5-methylisoquinolin-5-yl | MeO(CH₂)₃— | M⁺ + H: 422 (FAB) |
| 122 | phenyl—pyridine— | 5-methylisoquinolin-5-yl | MeNH— | M⁺ + H: 379 (FAB) |

(2)

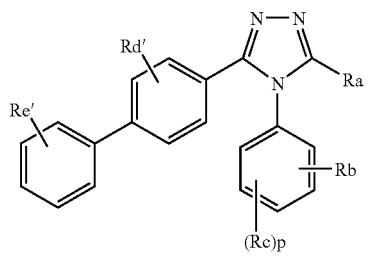

| Ex. | [D'-B'- structure] | A' | Ra | DATA: MS m/z |
|---|---|---|---|---|
| 123 | phenyl-pyridinyl-methyl | 5-methylisoquinolin-yl | EtNH— | M⁺ + H: 393 (FAB) |
| 124 | phenyl-pyridinyl-methyl | 5-methylisoquinolin-yl | Me₂N— | M⁺ + H: 393 (FAB) |
| 125 | phenyl-pyridinyl-methyl | 5-methylisoquinolin-yl | MeOCH₂CH₂N(H)— | M⁺ + H: 423 (FAB) |
| 126 | phenyl-pyridinyl-methyl | 5-methylisoquinolin-yl | MeOCH₂CH₂N(Me)— | M⁺ + H: 437 (FAB) |
| 127 | phenyl-pyridinyl-methyl | 5-methylisoquinolin-yl | (tetrahydrofuran-2-yl)CH₂N(H)— | M⁺ + H: 449 (FAB) |

(3)

| Ex | Ra | Rb | (Rc)p | Rd' | Re' | DATA: MS m/z |
|---|---|---|---|---|---|---|
| 128 | MeOCH₂— | 2-F | — | H | H | M⁺ + H: 360 (FAB) |
| 129 | HO₂CCH₂N(Me)CH₂— | 2-F | — | H | H | M⁺ + H: 417 (FAB) |
| 130 | MeO₂CCH₂N(Me)CH₂— | 2-F | — | H | H | M⁺ + H: 431 (FAB) |
| 131 | furan-2-yl | 2-F | — | H | H | M⁺ + H: 382 (FAB) |
| 132 | MeS- | 2-OMe | — | H | H | M⁺ + H: 374 (FAB) |
| 133 | EtS- | 2-OMe | — | H | H | M⁺ + H: 388 (FAB) |

-continued

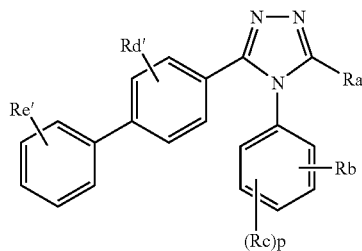

(3)

| Ex | Ra | Rb | (Rc)p | Rd' | Re' | DATA: MS m/z |
|---|---|---|---|---|---|---|
| 134 | Me(CH$_2$)$_2$S— | 2-F | — | H | H | M$^+$ + H: 390 (FAB) |
| 135 | Me(CH$_2$)$_4$S— | 2-F | — | H | H | M$^+$ + H: 418 (FAB) |
| 136 | Me(CH$_2$)$_6$S— | 2-F | — | H | H | M$^+$ + H: 446 (FAB) |
| 137 | CH$_2$=CHCH$_2$S— | 2-F | — | H | H | M$^+$ + H: 388 (FAB) |
| 138 | CH≡CCH$_2$S | 2-F | — | H | H | M$^+$ + H: 386 (FAB) |
| 139 | cHex-CH$_2$—S— | 2-F | — | H | H | M$^+$ + H: 444 (FAB) |
| 140 | cPr-CH$_2$—S— | 2-F | — | H | H | M$^+$ + H: 402 (FAB) |
| 141 | NCCH$_2$S— | 2-F | — | H | H | M$^+$ + H: 387 (FAB) |
| 142 | PhCH$_2$S— | 2-F | — | H | H | M$^+$ + H: 438 (FAB) |
| 143 | (2,6-di-Cl-Ph)CH$_2$S— | 2-F | — | H | H | M$^+$ + H: 506 (FAB) |
| 144 | (2-OMe-5-NO$_2$-Ph)CH$_2$S— | 2-F | — | H | H | M$^+$ + H: 513 (FAB) |
| 145 | (4-CO$_2$Me-Ph)CH$_2$S— | 2-F | — | H | H | M$^+$ + H: 496 (FAB) |
| 146 | 2-Py-CH$_2$—S— | 2-F | — | H | H | M$^+$ + H: 439 (FAB) |
| 147 | 3-Py-CH$_2$—S— | 2-F | — | H | H | M$^+$ + H: 439 (FAB) |
| 148 | 4-Py-CH$_2$—S— | 2-F | — | H | H | M$^+$ + H: 439 (FAB) |
| 149 | Ph(CH$_2$)$_2$S— | 2-F | — | H | H | M$^+$ + H: 452 (FAB) |
| 150 | H$_2$NC(O)CH$_2$S— | 2-F | — | H | H | M$^+$ + H: 405 (FAB) |
| 151 | Et$_2$N(CH$_2$)$_2$S— | 2-F | — | H | H | M$^+$ + H: 447 (FAB) |
| 152 | Me$_2$CHS— | 2-F | — | H | H | M$^+$ + H: 390 (FAB) |
| 153 | MeC(O)CH$_2$S— | 2-F | — | H | H | M$^+$ + H: 404 (FAB) |
| 154 | HO$_2$CCH$_2$S— | 2-F | — | H | H | M$^+$ + H: 406 (FAB) |
| 155 | Et$_2$NC(O)CH$_2$S— | 2-F | — | H | H | M$^+$ + H: 461 (FAB) |
| 156 | 2-Qin-CH$_2$—S— | 2-F | — | H | H | M$^+$ + H: 489 (FAB) |
| 157 | HO$_2$CCH$_2$N(Me)(CH$_2$)$_3$S— | 2-F | — | H | H | M$^+$ + H: 477 (FAB) |
| 158 | Me | 2-HO$_2$CCH$_2$N(Me)(CH$_2$)$_3$O— | — | H | H | M$^+$ + H: 457 (FAB) |
| 159 | Me | 2-CF$_3$ | — | H | H | M$^+$ + H: 380 (FAB) |
| 160 | Me | 2-OCF$_3$ | — | H | H | M$^+$ + H: 395 (FAB) |
| 161 | Me | 2-CO$_2$H | — | H | H | M$^+$ + H: 356 (FAB) |
| 162 | Me | 2-CONH$_2$ | — | H | H | M$^+$ + H: 355 (FAB) |
| 163 | Me | 2-CONMe$_2$ | — | H | H | M$^+$ + H: 383 (FAB) |
| 164 | Me | 2-pyrrol-1-yl | — | H | H | M$^+$ + H: 377 (FAB) |
| 165 | Me | 2-imidazol-1-yl | — | H | H | M$^+$ + H: 378 (FAB) |
| 166 | Me | 2-(1H-tetrazol-5-yl) | — | H | H | M$^+$ + H: 380 (FAB) |
| 167 | Me | 2-S(O)Me | — | H | H | M$^+$ + H: 374 (FAB) |
| 168 | Me | 2-SO$_2$Me | — | H | H | M$^+$ + H: 390 (FAB) |
| 169 | Me | 2-SO$_2$Ph | — | H | H | M$^+$ + H: 452 (FAB) |
| 170 | Me | 2-OMe | — | H | 3-F | M$^+$ + H: 360 (ESI) |
| 171 | Me | 2-OMe | — | H | 4-F | M$^+$ + H: 360 (ESI) |
| 172 | Me | 2-OMe | — | H | 2-Cl | M$^+$ + H: 376 (ESI) |
| 173 | Me | 2-OMe | — | H | 3-Cl | M$^+$ + H: 376 (ESI) |
| 174 | Me | 2-OMe | — | H | 4-Cl | M$^+$ + H: 376 (ESI) |
| 175 | Me | 2-OMe | — | H | 2-OMe | M$^+$ + H: 372 (ESI) |
| 176 | Me | 2-OMe | — | H | 3-OMe | M$^+$ + H: 372 (ESI) |
| 177 | Me | 2-OMe | — | H | 3-OEt | M$^+$ + H: 386 (ESI) |
| 178 | Me | 2-OMe | — | H | 4-OMe | M$^+$ + H: 372 (ESI) |
| 179 | Me | 2-OMe | — | H | 4-CF$_3$ | M$^+$ + H: 410 (ESI) |
| 180 | Me | 2-OMe | — | H | 4-OCF$_3$ | M$^+$ + H: 426 (ESI) |
| 181 | Me | 2-OMe | — | H | 3-NHAc | M$^+$ + H: 399 (ESI) |
| 182 | MeO(CH$_2$)$_2$— | 2-F | — | H | H | M$^+$ + H: 374 (FAB) |
| 183 | MeO(CH$_2$)$_3$— | 2-F | — | H | H | M$^+$ + H: 388 (FAB) |
| 184 | HO(CH$_2$)$_2$— | 2-F | — | H | H | M$^+$ + H: 360 (FAB) |
| 185 | HO(CH$_2$)$_3$— | 2-F | — | H | H | M$^+$ + H: 374 (FAB) |
| 186 | HO$_2$CCH$_2$N(Me)(CH$_2$)$_2$— | 2-F | — | H | H | M$^+$ + H: 431 (FAB) |
| 187 | HO$_2$CCH$_2$N(Me)(CH$_2$)$_3$— | 2-F | — | H | H | M$^+$ + H: 445 (FAB) |
| 188 | MeO-C(Me)$_2$-CH$_2$- | 2-F | — | H | H | M$^+$ + H: 402 (FAB) |
| 189 | HO-C(Me)$_2$-CH$_2$- | 2-F | — | H | H | M$^+$ + H: 388 (FAB) |

-continued

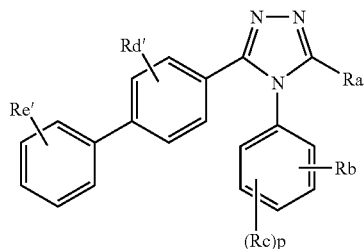

(3)

| Ex | Ra | Rb | (Rc)p | Rd' | Re' | DATA: MS m/z |
|---|---|---|---|---|---|---|
| 190 | NCCH$_2$— | 2-F | — | H | H | M$^+$ + H: 355 (FAB) |
| 191 | NC(CH$_2$)$_2$— | 2-F | — | H | H | M$^+$ + H: 369 (FAB) |
| 192 | ![NC-CH=CH-CH3] | 2-F | — | H | H | M$^+$ + H: 367 (FAB) |
| 193 | Ph-NH—CH$_2$— | 2-F | — | H | H | M$^+$ + H: 421 (FAB) |
| 194 | Ph-N(Me)—CH$_2$— | 2-F | — | H | H | M$^+$ + H: 435 (FAB) |
| 195 | 3-Py-O-CH$_2$— | 2-F | — | H | H | M$^+$ + H: 423 (FAB) |
| 196 | imidazol-1-yl-CH$_2$— | 2-F | — | H | H | M$^+$ + H: 396 (FAB) |
| 197 | Et$_2$NCH$_2$— | 2-F | — | H | H | M$^+$ + H: 401 (FAB) |
| 198 | piperidin-1-yl-ethyl | 2-F | — | H | H | M$^+$ + H: 413 (FAB) |
| 199 | morpholin-4-yl-ethyl | 2-F | — | H | H | M$^+$ + H: 415 (FAB) |
| 200 | 1,2,3,4-tetrahydroquinolin-1-yl-ethyl | 2-F | — | H | H | M$^+$ + H: 461 (FAB) |
| 201 | 1,2,3,4-tetrahydroisoquinolin-2-yl-ethyl | 2-F | — | H | H | M$^+$ + H: 461 (FAB) |
| 202 | 4,5,6,7-tetrahydrothieno[3,2-c]pyridin-5-yl-ethyl | 2-F | — | H | H | M$^+$ + H: 467 (FAB) |
| 203 | tetrahydropyran-4-yl-ethyl | 2-F | — | H | H | M$^+$ + H: 414 (FAB) |
| 204 | tetrahydrofuran-3-yl-methyl | 2-F | — | H | H | M$^+$ + H: 386 (FAB) |
| 205 | 1-benzyl-4-methylpiperidin-4-yl | 2-F | — | H | H | M$^+$ + H: 489 (FAB) |
| 206 | 4-methylpiperidin-4-yl | 2-F | — | H | H | M$^+$ + H: 399 (FAB) |

-continued

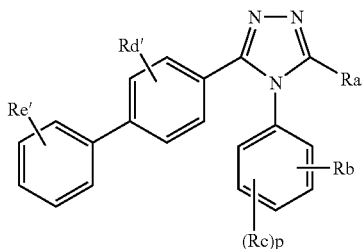

(3)

| Ex | Ra | Rb | (Rc)p | Rd' | Re' | DATA: MS m/z |
|---|---|---|---|---|---|---|
| 207 | H₂N— | 2-F | — | H | H | M⁺ + H: 331 (FAB) |
| 208 | MeNH— | 2-F | — | H | H | M⁺ + H: 345 (FAB) |
| 209 | EtNH— | 2-F | — | H | H | M⁺ + H: 359 (FAB) |
| 210 | Me(CH₂)₂NH— | 2-F | — | H | H | M⁺ + H: 373 (FAB) |
| 211 | Me(CH₂)₃NH— | 2-F | — | H | H | M⁺ + H: 387 (FAB) |
| 212 | Me₂CHNH— | 2-F | — | H | H | M⁺ + H: 373 (FAB) |
| 213 | Me₂CHCH₂NHMe | 2-F | — | H | H | M⁺ + H: 387 (FAB) |
| 214 | cyclobutyl-NHMe | 2-F | — | H | H | M⁺ + H: 385 (FAB) |
| 215 | cyclopentyl-NHMe | 2-F | — | H | H | M⁺ + H: 399 (FAB) |
| 216 | cyclohexyl-NHMe | 2-F | — | H | H | M⁺ + H: 413 (FAB) |
| 217 | Me₂NCH₂CH₂NHMe | 2-F | — | H | H | M⁺ + H: 402 (FAB) |
| 218 | MeSCH₂CH₂NHMe | 2-F | — | H | H | M⁺ + H: 405 (FAB) |
| 219 | HOCH₂CH₂NHMe | 2-F | — | H | H | M⁺ + H: 375 (FAB) |
| 220 | MeOCH₂CH₂NHMe | 2-F | — | H | H | M⁺ + H: 389 (FAB) |
| 221 | MeOCH(Me)CH₂NHMe | 2-F | — | H | H | M⁺ + H: 403 (FAB) |
| 222 | MeOCH(Et)CH₂NHMe | 2-F | — | H | H | M⁺ + H: 417 (FAB) |
| 223 | MeOCH₂CH₂NMe₂ | 2-F | — | H | H | M⁺ + H: 403 (FAB) |

-continued

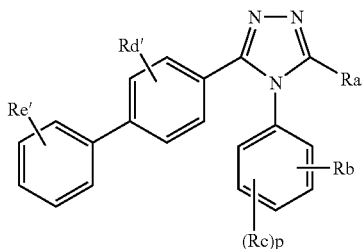

(3)

| Ex | Ra | Rb | (Rc)p | Rd' | Re' | DATA: MS m/z |
|---|---|---|---|---|---|---|
| 224 | MeO∼∼N(Me)∼Me | 2-F | — | H | H | M⁺ + H: 417 (FAB) |
| 225 | MeO∼∼N(Me)∼∼Me | 2-F | — | H | H | M⁺ + H: 431 (FAB) |
| 226 | MeO∼O∼∼NH | 2-F | — | H | H | M⁺ + H: 403 (FAB) |
| 227 | MeO∼(Me)O∼∼NH | 2-F | — | H | H | M⁺ + H: 417 (FAB) |
| 228 | EtOOC∼N(Me) | 2-F | — | H | H | M⁺ + H: 431 (FAB) |
| 229 | HOOC∼N(Me) | 2-F | — | H | H | M⁺ + H: 403(FAR) |
| 230 | Me∼∼O∼∼NH | 2-F | — | H | H | M⁺ + H: 417 (FAB) |
| 231 | MeO∼∼∼NH | 2-F | — | H | H | M⁺ + H: 403 (FAB) |
| 232 | (3-tetrahydrofuryl)-NH | 2-F | — | H | H | M⁺ + H: 401 (FAB) |
| 233 | (tetrahydrofuran-2-yl)methyl-NH | 2-F | — | H | H | M⁺ + H: 415 (FAB) |
| 234 | (S)-(tetrahydrofuran-2-yl)methyl-NH | 2-F | — | H | H | M⁺ + H: 415 (FAB) |
| 235 | (R)-(tetrahydrofuran-2-yl)methyl-NH | 2-F | — | H | H | M⁺ + H: 415 (FAB) |

-continued

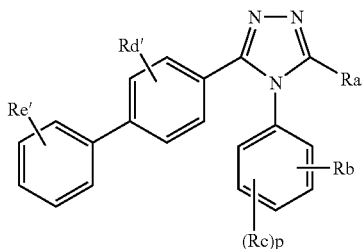

(3)

| Ex | Ra | Rb | (Rc)p | Rd' | Re' | DATA: MS m/z |
|---|---|---|---|---|---|---|
| 236 | (tetrahydrofuran-2-ylmethyl)(methyl)amino- | 2-F | — | H | H | $M^+ + H$: 429 (FAB) |
| 237 | (tetrahydropyran-4-yl)amino- | 2-F | — | H | H | $M^+ + H$: 415 (FAB) |
| 238 | (2-methoxycyclohexyl)amino- | 2-F | — | H | H | $M^+ + H$: 443 (FAB) |
| 239 | (pyridin-2-ylmethyl)amino- | 2-F | — | H | H | $M^+ + H$: 422 (FAB) |
| 240 | (pyridin-3-ylmethyl)amino- | 2-F | — | H | H | $M^+ + H$: 422 (FAB) |
| 241 | $Me_2N-$ | 2-F | — | H | H | $M^+ + H$: 359 (FAB) |
| 242 | $Et_2N-$ | 2-F | — | H | H | $M^+ + H$: 387 (FAB) |
| 243 | Et(Me)N-Me | 2-F | — | H | H | $M^+ + H$: 373 (FAB) |
| 244 | morpholin-4-yl- | 2-F | — | H | H | $M^+ + H$: 401 (FAB) |
| 245 | imidazol-1-yl- | 2-F | — | H | H | $M^+ + H$: 382 (FAB) |
| 246 | 2-methylimidazol-1-yl- | 2-F | — | H | H | $M^+ + H$: 396 (FAB) |
| 247 | $CH_3CONH-$ | 2-F | — | H | H | $M^+ + H$: 373 (FAB) |
| 248 | $CH_3SO_2NH-$ | 2-F | — | H | H | $M^+ + H$: 409 (FAB) |
| 249 | MeO— | 2-F | — | H | H | $M^+ + H$: 346 (FAB) |
| 250 | EtO— | 2-F | — | H | H | $M^+ + H$: 360 (FAB) |
| 251 | MeS— | 2-F | — | H | H | $M^+ + H$: 362 (FAB) |
| 252 | EtS— | 2-F | — | H | H | $M^+ + H$: 376 (FAB) |
| 253 | $MeSO_2-$ | 2-F | — | H | H | $M^+ + H$: 394 (FAB) |
| 254 | Me | 3-$CF_3$ | — | H | H | $M^+ + H$: 380 (FAB) |
| 255 | Et | 3-$CF_3$ | — | H | H | $M^+ + H$: 394 (FAB) |

-continued

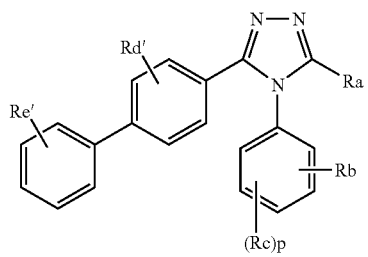

(3)

| Ex | Ra | Rb | (Rc)p | Rd' | Re' | DATA: MS m/z |
|---|---|---|---|---|---|---|
| 256 | Me | 2-NO$_2$ | — | H | H | M$^+$ + H: 357 (FAB) |
| 257 | Me | 2-NHOH | — | H | H | M$^+$ + H: 343 (FAB) |
| 258 | Me | 2-NHCOMe | — | H | H | M$^+$ + H: 369 (FAB) |
| 259 | Me | 2-NHCOPh | — | H | H | M$^+$ + H: 431 (FAB) |
| 260 | Me | 2-2-NHSO$_2$Me | — | H | H | M$^+$ + H: 405 (FAB) |
| 261 | Me | 2-NHSO$_2$Ph | — | H | H | M$^+$ + H: 467 (FAB) |
| 262 | Me | 2-CO$_2$Me | — | H | H | M$^+$ + H: 370 (FAB) |
| 263 | Me$_2$CH— | 2-CO$_2$Me | — | H | H | M$^+$ + H: 398 (FAB) |
| 264 | MeO-CH$_2$CH$_2$-N(Me)- | 2-Br | — | H | H | M$^+$ + H: 463 (FAB) |
| 265 | (tetrahydrofurfuryl)NH— | 2-Br | — | H | H | M$^+$ + H: 475 (FAB) |
| 266 | Me | 2-CN | — | H | H | M$^+$ + H: 337 (FAB) |
| 267 | Et | 2-CN | — | H | H | M$^+$ + H: 351 (FAB) |
| 268 | Me$_2$N— | 2-CN | — | H | H | M$^+$ + H: 366 (FAB) |
| 269 | MeO-CH$_2$CH$_2$-N(Me)- | 2-CN | — | H | H | M$^+$ + H: 410 (FAB) |
| 270 | Et | 3-CN | — | H | H | M$^+$ + H: 351 (FAB) |
| 271 | Et | 3-NHCOMe | 2-Me | H | H | M$^+$ + H: 397 (FAB) |
| 272 | Et | 3-COOMe | 2-Me | H | H | M$^+$ + H: 398 (FAB) |
| 273 | Et | 3-CONH$_2$ | 2-Me | H | H | M$^+$ + H: 383 (FAB) |
| 274 | Et | 3-CH$_2$-OH | 2-Me | H | H | M$^+$ + H: 370 (FAB) |
| 275 | Et | 3-CH$_2$OMe | 2-Me | H | H | M$^+$ + H: 384 (FAB) |
| 276 | Et | 3-CH$_2$NMe$_2$ | 2-Me | H | H | M$^+$ + H: 397 (FAB) |
| 277 | Et | 3-CH$_2$-CN | 2-Me | H | H | M$^+$ + H: 379 (FAB) |
| 278 | Et | 3-CONH$_2$ | 2-Cl | H | H | M$^+$ + H: 403 (FAB) |
| 279 | Et | 2-(3-Py-O-) | — | H | H | M$^+$ + H: 419 (FAB) |
| 280 | Et | 2-(2-Py-O-) | — | H | H | M$^+$ + H: 419 (FAB) |
| 281 | Et— | 2-F | — | 2-OMe | H | M$^+$ + H: 374 (FAB) |
| 282 | Et— | 2-F | — | 2-OH | H | M$^+$ + H: 360 (FAB) |
| 283 | Et— | 2-F | — | 3-OMe | H | M$^+$ + H: 374 (FAB) |
| 284 | Et— | 2-F | — | 3-OH | H | M$^+$ + H: 360 (FAB) |
| 285 | CF$_3$— | 2-F | — | H | H | M$^+$ + H: 384 (FAB) |
| 286 | CF$_3$— | 2-F | — | 2-OMe | H | M$^+$ + H: 414 (FAB) |
| 287 | CF$_3$— | 2-F | — | 3-Me | H | M$^+$ + H: 398 (FAB) |
| 288 | CF$_3$CH$_2$— | 2-F | — | H | H | M$^+$ + H: 398 (FAB) |

INDUSTRIAL APPLICABILITY

The pharmaceutical drug of the invention has an action to inhibit the activity of glycine transporter and an activity to activate the function of the NMDA receptor. Thus, the pharmaceutical drug of the invention is useful as a therapeutic agent of dementia, schizophrenia, cognitive disorders, or cognitive disorders involved in various diseases such as Alzheimer disease, Parkinson's disease or Huntington disease or the like, or spasm involved in diseases such as nerve degenerative diseases and cerebrovascular disorders, or the like. Particularly, the pharmaceutical drug is useful for the amelioration of learning disability of dementia and the like.

The invention claimed is:

1. A pharmaceutical composition for glycine transporter inhibitor which comprises a triazole compound represented by the following formula (I) or a pharmaceutically acceptable salt thereof as the effective ingredient:

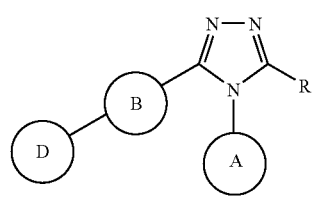
(I)

in the formula, the symbols represent the following meanings;
Ring A:
(1) an aromatic carbon ring which may be substituted,
(2) an aliphatic carbon ring which may be substituted and may be condensed with benzene ring or hetero ring, or
(3) a 6-membered hetero ring which may be substituted and contain one nitrogen atom as a ring atom and may contain one oxygen atom or sulfur atom as a hetero atom other than the nitrogen atom and may be condensed with benzene ring;

Ring B or D may be the same or different and each represents aromatic carbon ring which may be substituted, an aliphatic carbon atom which may be substituted, or a hetero ring which may be substituted;

R: H, halogeno-lower alkyl, aryl which may be substituted, hetero ring which may be substituted, cycloalkyl which may be substituted, or -[Alk1]m-X-[Alk2]n-Y—R$^1$ wherein R$^1$: H, OH, cyano, aryl which may be substituted, hetero ring which may be substituted, cycloalkyl which may be substituted, or lower alkoxyl;

X: bond, oxygen atom, S(O)q, or —N(R$^2$)—;
Y: bond, —C(O)—, —C(O)—N(R$^3$)—, -Z$_1$-Alk3-, or —N(R$^3$)—Alk3-C(O)—, with the proviso that R$^1$ represent other than OH and lower alkoxy, when Y is bond;
Alk1 or Alk2 may be the same or different and each represents lower alkylene, lower alkenylene or lower alkynylene; and m or n may be the same or different and each represents 0 or 1 or m+n=1, provided that X represents bond;
Z$_1$: S(O)q, —N(R$^3$)—, —C(O)— or —C(O)—N(R$^3$)—;
Alk3: lower alkylene;
R$^2$ or R$^3$: the same or different from each other and each represents H or lower alkyl;
q: may be 0, 1 or 2.

2. A pharmaceutical composition for ameliorating learning disability according to claim 1.

3. A triazole compound represented by the following formula (Ia) or a salt thereof:

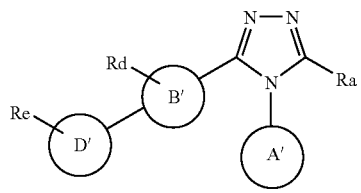
(Ia)

in the formula, the symbols represent the following meanings;
Ring A':
(1) the group represented by the formula:

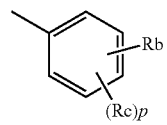

(2) naphthalene which may be substituted with one or two substituents selected from the group represented by Rf,
(3) an aliphatic carbon ring which may be substituted with one or two substituents selected from the group represented by Rf and which may be condensed with benzene ring or hetero ring, or
(4) a 6-membered hetero ring which may be substituted with one or two substituents selected from the group represented by Rf and which contain one nitrogen atom as the ring atom and may contain one oxygen atom or sulfur atom as a hetero atom other than the nitrogen atom and may be condensed with benzene ring;

Ring B': benzene or nitrogen-containing monocyclic hetero ring; or
Ring D': benzene or hetero ring, provided that ring A', B' and D' never simultaneously represents benzene ring;
Ra: a halogeno-lower alkyl, a hetero ring which may be substituted, cycloalkyl which may be substituted, or -[Alk1]m-X-[Alk2]n-Y—R$^1$ wherein
R$^1$: H, OH, cyano, aryl which may be substituted, hetero ring which may be substituted, cycloalkyl which may be substituted, or lower alkoxyl;

X: bond, oxygen atom, S(O)q, or —N(R$^2$)—;
Y: bond, —C(O)—, —C(O)—N(R$^3$)—, -Z$_1$-Alk3-, or —N(R$^3$)-Alk3—C(O)—, with the proviso that R$^1$ represent other than OH and lower alkoxy, when Y is bond;
Alk1 or Alk2 may be the same or different and each represents lower alkylene, lower alkenylene, or lower alkynylene;
m or n may be the same or different and each represents 0 or 1 or m+n=1, provided that X represents bond;
Z$_1$: S(O)q, —N(R$^3$)—, —C(O)— or —C(O)—N(R$^3$)—;
Alk3: lower alkynylene;
R$^2$ or R$^3$: the same or different from each other and each represents H, or lower alkyl;
Rb: halogen atom, lower alkyl which may be substituted with the following substituents, lower alkynyl, halogeno-lower alkyl, hetero ring, hetero ring-O—, cyano, nitro, halogeno-lower alkyl-O—, lower alkoxyl, —O-lower alkylene-N(R$^3$)-lower alkylene-C(O)O—R$^6$, Z$_2$-R$^6$, or Z$_3$-R$^7$, the substituents of the lower alkyl: OH, cyano, lower alkoxyl, amino which may be substituted with lower alkyl;

Z$_2$: S(O)q, —N(R$^3$)—, —C(O)—, —C(O)—N(R$^3$)—, —N(R$^3$)—C(O)—, —C(O)—S(O)q-, —N(R$^3$)—S(O)q-, or —C(O)O—;
Z$_3$: —N(R$^3$)—, or —N(R$^3$)—C(O)—;
R$^6$: H, lower alkyl or aryl;
R$^7$: OH, or lower alkoxyl;
p: 0 or 1;
q: 0, 1 or 2;
Rc: lower alkyl, or halogen atom;
Rd or Re: the same or different from each other and each represents H, halogen atom, lower alkyl, lower alkoxyl, OH, lower alkyl, halogeno-lower alkyl, phenyl, halogeno-lower alkyl-O—, amino which may be substituted with lower alkyl or —NR$^8$C(O)—R$^9$;

R⁸ or R⁹: the same or different from each other and each represents H, or lower alkyl;

Rf: a group represented by Rb, oxo group, or aryl, with the proviso that Rd represents other than H, when the ring A' represents benzene substituted with lower alkoxyl and the ring B' represents benzene.

4. A triazole compound represented by the following formula (Ib) or a salt thereof:

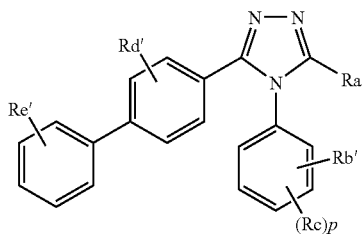

(Ib)

in the formula, the symbols represent the following meanings:

Ra: a halogeno-lower alkyl, a hetero ring which may be substituted, cycloalkyl which may be substituted, or -[Alk1]m-X-[Alk2]n-Y—R¹ wherein

R¹: H, OH, cyano, aryl which may be substituted, hetero ring which may be substituted, cycloalkyl which may be substituted, or lower alkoxyl;

X: bond, oxygen atom, S(O)q, or —N(R²)—;

Y: bond, —C(O)—, —C(O)—N(R³)—, -Z₁-Alk3-, or —N(R³)—Alk3-C(O)—, with the proviso that R¹ represent other than OH and lower alkoxy, when Y is bond;

Alk1 or Alk2 may be the same or different and each represents lower alkylene, lower alkenylene, or lower alkynylene;

m or n may be the same or different and each represents 0 or 1 or m+n=1, provided that X represents bond;

Z₁: S(O)q, —N(R³)—, —C(O)— or —C(O)—N(R³)—;

Alk3: lower alkynylene;

R² or R³: the same or different from each other and each represents H, or lower alkyl;

Rb': halogen atom, lower alkyl which may be substituted with the following substituents, halogeno-lower alkyl, hetero ring, hetero ring-O—, cyano, nitro, halogeno-lower alkyl-O—, lower alkoxyl, —O-lower alkylene-N(R³)-lower alkylene-C(O)O—R⁶, —N(R³)—R⁷, Z₂'-R⁶, or Z₃-R⁷;

the substituents of the lower alkyl: OH, cyano, lower alkoxyl, amino which may be substituted with lower alkyl;

Z₂': S(O)q, —C(O)—, —C(O)—N(R³)—, —N(R³)—C(O)—, —C(O)—S(O)q-, —N(R³)—S(O)q-, —C(O)O;

Z₃: —N(R³)—, or —N(R³)—C(O)—;

R⁶: H, lower alkyl or aryl;

R⁷: OH, or lower alkoxyl;

p: 0 or 1;

q: 0, 1 or 2;

Rc: lower alkyl, or halogen atom;

Rd': H, lower alkoxyl, OH or lower alkyl;

Re': H, halogen atom, lower alkoxyl, halogeno-lower alkyl, halogeno-lower alkyl-O—, or NR⁸C(O)—R⁹;

R⁸ or R⁹: the same group as formula (Ia) described in the claim 3; with the proviso that, (1) at least one of Rd' or Re' represents a group other than H, when Ra is lower alkyl, p=0:

Rb' represents lower alkyl, lower alkoxyl or halogen atom; or Rd' represents a group except for lower alkyl, provided that Re' is H;

(2) Rb' represents a group other than lower alkyl or lower alkoxyl, when Ra represents α-styryl and Rd' and Re' represent H and p=0;

(3) Rb' represents a group other than lower alkyl, when Ra represents 2 furyl and Rd' and Re' represent H and p=0.

5. A triazole compound or a salt thereof according to claim 3, wherein in the triazole derivative represented by the general formula (Ia), the ring B' represents nitrogen-containing monocyclic hetero ring; the ring D' is benzene ring; Rf is halogen atom, lower alkyl, lower alkoxyl, aryl, cyano, carbamoyl or oxo group.

6. A compound selected from the group consisting of 5-[4-(2,6-Difluorophenyl)-5-isopropyl-4H-1,2,4-triazol-3-yl]-2-phenylpyridine; 4-[3-isopropyl-5-(6-phenylpyridin-3-yl)-4H-1,2,4-triazol-4-yl]-2,1,3-benzooxadiazole; 3-[3-(3-methoxypropyl)-5-(6-phenylpyridin-3-yl)-4H-1,2,4-triazol-4-yl]-2-methylbenzonitrile; 3-[3-ethyl-5-(6-phenylpyridin-3-yl)-4H-1,2,4-triazol-4-yl]-2-methylbenzonitrile; 2-{3-[N-(2-methoxyethyl)-N-methylamino]-5-(6-phenylpyridin-3-yl)-4H-1,2,4-triazol-4-yl}benzonitrile; and 4-(2,1,3-benzooxadiazol-4-yl)-N-(2-methoxyethyl)-N-methyl-5-(6-phenylpyridin-3-yl)-4H-1,2,4-triazol-3-ylamine or a salt thereof.

7. A pharmaceutical composition which comprises the triazole compound of claim 3 or 4 as an active ingredient.

* * * * *